(12) United States Patent
Harrison et al.

(10) Patent No.: US 11,702,457 B2
(45) Date of Patent: Jul. 18, 2023

(54) AGENT AND METHOD FOR ENHANCING FERTILITY

(71) Applicant: MONASH UNIVERSITY, Clayton (AU)

(72) Inventors: Craig Anthony Harrison, Clayton (AU); Kelly Louise Walton, Clayton (AU)

(73) Assignee: Monash University, Victoria (AU)

( * ) Notice: Subject to any disclaimer, the term of this patent is extended or adjusted under 35 U.S.C. 154(b) by 99 days.

(21) Appl. No.: 17/053,856

(22) PCT Filed: May 9, 2019

(86) PCT No.: PCT/AU2019/000054
§ 371 (c)(1),
(2) Date: Nov. 9, 2020

(87) PCT Pub. No.: WO2019/213690
PCT Pub. Date: Nov. 14, 2019

(65) Prior Publication Data
US 2021/0115098 A1    Apr. 22, 2021

(30) Foreign Application Priority Data

May 9, 2018    (AU) ............................... 2018901579

(51) Int. Cl.
*A61K 38/00* (2006.01)
*C07K 14/475* (2006.01)
*C12N 5/075* (2010.01)

(52) U.S. Cl.
CPC .......... *C07K 14/475* (2013.01); *C12N 5/0609* (2013.01); *A61K 38/00* (2013.01); *C12N 2501/19* (2013.01)

(58) Field of Classification Search
CPC .... C07K 14/475; C07K 14/495; A61K 38/00; A61K 38/18; C12N 2501/19; C12N 5/0609; C12N 5/0682; A61P 15/08
See application file for complete search history.

(56) References Cited

FOREIGN PATENT DOCUMENTS

| WO | WO 2003/102199 | 12/2003 |
|---|---|---|
| WO | WO 2006/059913 | 6/2006 |
| WO | WO 2006/059914 | 6/2006 |
| WO | WO 2007/009166 | 1/2007 |
| WO | WO 2010/130008 | 11/2010 |
| WO | WO 2014/018404 | 1/2014 |

OTHER PUBLICATIONS

Simpson et al. (Endocrinology 153: 1301-1310, 2012). Activation of Latent Human GDF9 by a Single Residue Change (Gly391Arg) in the Mature Domain (Year: 2012).*
Gilchrist et al. "Oocyte maturation and quality: role of cyclic nucleotides," Reproduction, 2016, vol. 152, No. 5, pp. R143-R157.
Mottershead et al. "Cumulin, an Oocyte-secreted Heterodimer of the Transforming Growth Factor-β Family, Is a Potent Activator of Granulosa Cells and Improves Oocyte Quality," Journal of Biological Chemistry, Sep. 2015, vol. 290, No. 39, pp. 24007-24020.
Peng et al. "Growth differentiation factor 9:bone morphogenetic protein 15 heterodimers are potent regulators of ovarian functions," PNAS, 2013, vol. 110, No. 8, pp. E776-E785.
International Search Report and Written Opinion for International (PCT) Patent Application No. PCT/AU2019/000054, dated Jun. 26, 2019, 10 pages.
Li et al. "Modifications of Human Growth Differentiation Factor 9 to Improve the Generation of Embryos From Low Competence Oocytes," Molecular Endocrinology, Jan. 2015, vol. 29, No. 1, pp. 40-52.
Stocker et al. "A variant of human growth differentiation factor-9 that improves oocyte developmental competence," Journal of Biological Chemistry, Jun. 2020, vol. 295, No. 23, pp. 7981-7991.
Extended Search Report for European Patent Application No. 19798972.6, dated May 11, 2022, 13 pages.

* cited by examiner

*Primary Examiner* — Aradhana Sasan
*Assistant Examiner* — Mercy H Sabila
(74) *Attorney, Agent, or Firm* — Sheridan Ross P.C.

(57) ABSTRACT

An agent capable of promoting proliferation and differentiation of granulosa cells is disclosed which comprises a growth and differentiation factor-9 (GDF9) protein comprising a modified GDF9 polypeptide monomer which includes at least one amino acid substitution that enhances binding to and/or activation of activin-like kinase 4 and/or 5 receptor (ALK4/5). The agent is preferably provided in a mature dimeric form (eg comprising two monomers of the same modified GDF9 polypeptide monomer) and/or in a pro/mature complex form. The agent may be suitable for, inter alia, promoting oocyte maturation in vitro for use in assisted reproductive technologies.

19 Claims, 6 Drawing Sheets
Specification includes a Sequence Listing.

```
hGDF9   350 QNECELHDFRLSFSQLKWDNWIVAPHRYNPRYCKGDCPRAVGHRYGSPVHTMVQNIIYEK 409
                         *
hBMP15  288 NNQCSLHPFQISFRQLGWDHWIIAPPFYTPNYCKGTCLRVLRDGLNSPNHAIIQNLINQL 347
                                                                  * hGDF9   410 LDSSVPRPSCVPAKYSPLSVLTIEPDGSIAYKEYEDMIATKCTCR 454 (SEQ ID NO: 19)

hBMP15  348 VDQSVPRPSCVPYKYVPISVLMIEANGSILYKEYEGMIAESCTCR 392 (SEQ ID NO: 20)
```

AGENT AND METHOD FOR ENHANCING FERTILITY

CROSS-REFERENCE TO RELATED APPLICATIONS

This application is a national stage application under 35 U.S.C. 371 and claims the benefit of PCT Application No. PCT/AU2019/000054 having an international filing date of 9 May 2019, which designed the United States, which PCT application claimed the benefit of Australian Provisional Patent Application No 2018901579 titled "Agent and method for enhancing fertility" filed on 9 May 2018, the contents of each of which are hereby incorporated by reference in their entireties.

REFERENCE TO SEQUENCE LISTING

This application contains a Sequence Listing submitted as an electronic text file named "48949PCTSeq_Listing_Project_ST25_2321457_1.txt", having a size in bytes of 9000 bytes, and created on 2018 May 9. The information contained in this electronic file is hereby incorporated by reference in its entirety pursuant to 37 CFR § 1.52(e)(5).

TECHNICAL FIELD

The present disclosure relates to the field of fertility and methods for treating infertility. Particularly, the present disclosure relates to a novel agent and method that may be suitable for, inter alia, promoting oocyte maturation in vitro.

BACKGROUND

The reasons for infertility in women are numerous but mostly broadly relate to ovulation disorders, damage to the fallopian tubes (tubal infertility), and uterine or cervical causes such as endometriosis.

It has been estimated that ovulation disorders are the cause of infertility in around 25% of infertile couples (see Fertility: Assessment and Treatment for People with Fertility Problems, Royal College of Obstetricians & Gynaecologists (London), February 2013). Ovulation disorders are characterised by infrequent or no ovulation arising typically from poor or incomplete folliculogenesis such that the expulsion of the oocyte from the mature follicle (ie ovulation) of the ovary is not reached or only occasionally. Common causes include polycystic ovary syndrome (PCOS) and hypothalamic dysfunction which are both associated with dysregulation of reproductive hormones from the hypothalamus and pituitary gland (ie follicle stimulating hormone (FSH) and luteinising hormone (LH)) which stimulate ovulation. However, in addition, the oocyte itself is also known to play an important role in regulating and promoting follicle growth, and thereby its own development, by the production of two key oocyte-derived growth factors, namely growth and differentiation factor-9 (GDF9) and bone morphogenetic protein-15 (BMP-15). These two growth factors, which both belong to the TGF-β superfamily, appear to predominantly act on supporting granulosa cells (where they cause proliferation and differentiation of the cells into cumulus cells which have a role in the coordination of follicular development and oocyte maturation (Fauser et al. 2010)), however their precise roles in ovarian function, and particularly folliculogenesis, are yet to be fully elucidated. Nevertheless, in women at least, it is considered that both GDF9 and BMP15 are essential for normal ovarian function since heterozygous mutations of their respective genes have been found in women with primary ovarian insufficiency (POI (Di Pasquale et al. 2004; Patino et al. 2017; Dixit et al. 2005) thereby linking abnormal levels of these growth factors to the disorder and poor folliculogenesis.

Further studies into the role of GDF9 and BMP15 have found inter ala that:

(i) In women, hGDF9 on its own is latent (ie inactive), whilst in mice it has been found that mGDF9 is able to dose-dependently induce Sma- and Mad-related proteins (Smad)-2/3 signalling (Simpson el al. 2012);

(ii) When granulosa cells are treated with ovine GDF9 (oGDF9) alone, there is no obvious biological affect, but when co-treated with ovine BMP15 (oBMP15), the granulosa cells proliferate and differentiate (McNatty et al. 2005), and these effects appear to be mediated by Smad-2/3 signalling as they are blocked by the use of an ALK4/5/7 kinase inhibitor (McIntosh et al. 2008);

(iii) hBMP15 is able to dose-dependently induce Smad-1/5/8 signalling via ALK6 activation (Al-Musawi et al. 2013), but hBMP5 treatment alone does not induce the expression of genes associated with cumulus expansion or stimulation of granulosa cell proliferation (Mottershead et al. 2015); and (iv) Treatment of granulosa cells with a hGDF9:hBMP15 heterodimer leads to a dramatic increase in expression of cumulus expansion-associated genes, which can be blocked with an ALK4/5/7 inhibitor, and which is largely unaffected by the presence of an ALK2/3/6 inhibitor (Peng et al. 2013).

The latter finding is particularly interesting in that it indicates that activation of Smad-1/5/8 signalling by hBMP15 is likely only a secondary role, with its primary role being the activation of hGDF9. Indeed, it is conceivable that the only role of BMP15 may be to form the heterodimer with GDF9, now known as cumulin, in order to more potently activate Smad-2/3 signalling for the purpose of promoting cumulus expansion (Peng et al. supra; Mottershead et al. supra). Comparative testing with cumulus cell expansion assays has shown that the murine GDF9:BMP15 heterodimer is about 10- to 30-fold more active than the murine GDF9 homodimer, and that the human GDF9:BMP15 heterodimer is a staggering 1000- to 3000-fold more active than human BMP15 homodimer (remembering that hGDF9 is latent) (Peng et al. supra).

Recognising that cumulin (GDF9:BMP15 heterodimer) is highly bioactive and appears to promote follicle development and oocyte maturation via potent Smad-2/3 signalling used to stimulate granulosa cells (eg for their important role in promoting oocyte maturation) (Mottershead et al. supra), it is considered that this molecule may have important implications for improving fertility in women and other female mammals. In this regard, some work has been conducted with cumulin to determine whether it may be beneficial in assisted reproductive technology (ART), and early experimentation has demonstrated that Pro-cumulin (ie a pro/mature heterodimeric complex of GDF9 and BMP15) enhanced embryo development when used during in vitro maturation (IVM) of porcine cumulus-oocyte-complexes (COCs)(Mottershead et al. supra).

IVM is a type of assisted reproductive technology used in conjunction with in vitro fertilisation (IVF). A key difference between the two methods is the use of exogenous hormones to stimulate the ovaries. That is, conventional IVF involves hyperstimulation using exogenous gonadotrophins to mature the oocyte in vivo, following which mature COCs are collected and the oocyte(s) then fertilised. In contrast, IVM requires minimal or no use of exogenous gonadotrophins.

Rather, small antral stage follicles are collected and punctured to release immature COCs. The COCs are then cultured in vitro under conditions favourable to oocyte maturation for 24 to 40 hours, after which the oocyte(s) are then fertilised. With the risk of developing ovarian hyperstimulation syndrome (OHSS) almost entirely removed, IVM has the potential to address a number of clinical conditions which normally affect the development of a successful pregnancy. For example, to correct ex vivo the abnormal follicle development which occurs with polycystic ovary syndrome (PCOS) prior to IVF, or when utilising immature oocytes stored as part of a fertility preservation strategy prior to destructive cancer therapies (Smitz et al. 2011). Additionally, IVM is not restricted only to use for humans. It is an accepted and utilised technology for the breeding of domestic animals with beneficial outcomes for agriculture, such as the breeding of cattle and sheep with commercially desirable traits.

However, to date, IVM has not entered mainstream clinical use due to lower success rates than that currently achieved with conventional IVF (Gilchrist 2011). The use of human Pro-cumulin as an IVM additive may provide an effective starting point towards improving the current success rates (Mottershead et al. supra), but unfortunately, the recombinant production of this protein necessary for its widespread use is currently complicated by a number of factors.

First, the co-expression of both hGDF9 and hBMP15 has some limitations. That is, it has been found that co-transfecting host expression cells with two recombinant plasmids encoding hGDF9 and hBMP15 leads to a reduction in the level of expression of the two proteins relative to when hGDF9 and hBMP15 are expressed alone, thereby inhibiting the ability to generate large quantities easily. Also, based on the distribution and transfection efficiency of cells, co-transfection also often results in the production of a complex mixture comprising GDF9 homodimers, BMP15 homodimers as well as the desired cumulin heterodimer. As the monomer proteins of all of these three dimer forms are non-covalently associated, the ratio of each dimer in a cumulin preparation is unable to be readily determined (nb. analysis via SDS-PAGE results in the dimers separating into the monomeric mature constituent proteins) and, thus far, the only way found to successfully confirm the presence of Pro-cumulin in a co-purified preparation containing both hGDF9 and hBMP15 is to assess the Smad-2/3 activity (Mottershead et al. supra). This leads to the second complicating factor; as shown in the Examples hereinafter, different preparations (ie batches) of Pro-cumulin vary in their potency when assessed by GDF9 concentration. This is very likely due to the batches containing different ratios of Pro-cumulin to Pro-GDF9 homodimer and it would therefore seem that in order to make a potent Pro-cumulin preparation it is necessary to first optimise the ratios of the hGDF9 and hBMP15 so as to favour Pro-cumulin formation instead of the Pro-GDF9 homodimer. However, further, it may also be important to limit the formation of the Pro-BMP15 homodimer, since any excessive Smad-1/5/8 signalling that might be caused by the Pro-BMP15 homodimer might have an adverse effect on follicle health since it has been reported that in mice, a 5-fold increase in mBMP15 resulted in an increased number of atretic antral follicles which was followed by an early onset of acyclicity (McMahon et al. 2008). Accordingly, the risk of a significant presence of Pro-BMP15 homodimers is a further complicating factor in the preparation of cumulin and its potential use in ART.

There is thus a need to develop a viable method to produce cumulin preparations comprising significant and consistent amounts of the Pro-cumulin or cumulin proteins (preferably free of, or including only minimal amounts of GDF9 and/or BMP15 homodimers), or otherwise determine an alternative approach to investigating and making use of cumulin activity in assisted reproductive technology such as IVM.

SUMMARY

According to a first aspect of the present disclosure, there is provided an agent capable of promoting proliferation and differentiation of granulosa cells, said agent comprising a growth and differentiation factor-9 (GDF9) protein comprising a modified GDF9 polypeptide monomer which includes at least one amino acid substitution that enhances binding to and/or activation of activin-like kinase 4 and/or 5 receptor (ALK4/5).

The modified GDF9 polypeptide monomer is preferably derived from human GDF9 (hGDF9) and preferably includes one or more of the following amino acid substitutions:
(i) S363R, S363K or S363H;
(ii) K366G, K366A, K366V, K366I, K366L or K366M; and
(iii) N369H, N369K or N369R.

In a second aspect, the present disclosure provides a composition, preferably an aqueous composition, comprising the agent of the first aspect optionally in combination with a pharmacologically acceptable carrier (eg solvent and/or buffer) and/or excipient.

In a third aspect, the present disclosure provides a method of promoting proliferation and differentiation of granulosa cells (preferably m vitro), said method comprising contacting granulosa cells with an effective amount of the agent of the first aspect or the composition of the second aspect.

In a related fourth aspect, the present disclosure provides the use of an agent of the first aspect or the composition of the second aspect for promoting proliferation and differentiation of granulosa cells.

Further, in a fifth aspect, the present disclosure provides the use of an agent of the first aspect in the manufacture of a composition for promoting proliferation and differentiation of granulosa cells.

Still further, in a sixth aspect, the present disclosure provides a method of promoting oocyte maturation (preferably in vitro), said method comprising contacting an immature cumulus-oocyte-complex (COC) with an effective amount of the agent of the first aspect or the composition of the second aspect.

In a seventh aspect, the present disclosure provides the use of an agent of the first aspect or the composition of the second aspect for promoting oocyte maturation.

In an eighth aspect, the present disclosure provides the use of an agent of the first aspect in the manufacture of a composition for promoting oocyte maturation.

DETAILED DESCRIPTION

Figures 1, 2:
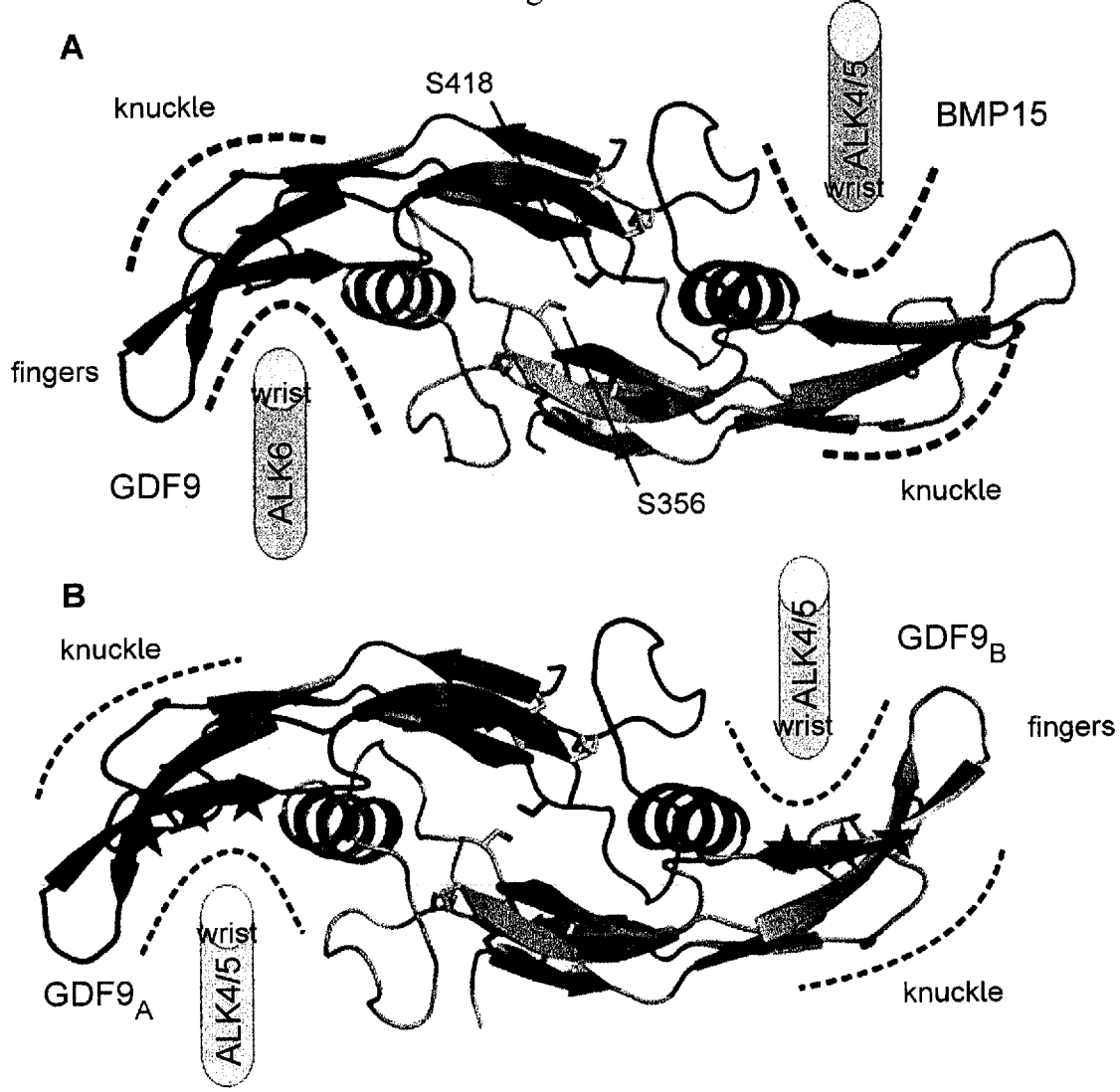
FIG. 1 depicts ribbon plot molecular models of mature human cumulin and mature human GDF9 with probable type 1 receptor binding sites indicated (within the "wrists"; the wrist of each monomer is formed by an α-helix region): (A) human cumulin—the GDF9 (dark) and BMP15 (light) monomers both contribute to the formation of the type I receptor binding sites of mature cumulin, with opposite sides of each monomer forming two different type 1 receptor binding sites on each side of the cumulin protein. This confers cumulin with the characteristic of activating both Smad signalling pathways; cumulin uses one ALK6 receptor to moderately activate the Smad-1/5/8 signalling pathway, and more importantly, the opposite site binds ALK4/5 with high affinity to potently activate the Smad-2/3 signalling pathway. (B) human GDF9—both monomers of the mature GDF9 homodimer contribute to the formation of the type 1 receptor binding sites which are identical on either side of the protein. When separated from its propeptide, these sites bind ALK4/5 with very low affinity to mildly activate the Smad-213 signalling pathway. As described hereinafter, it was found that the substitution of three amino acids (stars) in the probable type 1 receptor binding sites of the protein generated two ALK4/5 binding sites with high affinity. Figure modified from Mottershead et al. supra.
FIG. 2 provides an amino acid sequence alignment of a C-terminal portion of the mature hGDF9 and mature hBMP15 polypeptides (ie the mature domains). The sequences are 59% identical. The amino acids predicted to be involved with type 1 receptor binding by hGDF9 are indicated. The underlined amino acids indicate the probable type 1 receptor binding site of monomer 1 (wrist). The underlined and bolded amino acids indicate the probable type 1 receptor binding site of monomer 2 ("fingers"; the fingers 1 and 2 are formed from 0-sheets within the monomer structure). The site in cumulin which binds ALK4/5 with high affinity is predicted to be composed of the wrist of hBMP15 (monomer 1) and the fingers of hGDF9 (monomer 2). There are five amino acid differences between hGDF9 and hBMP15 within the wrist. Using the numbering for hGDF9, these are S363R, K366G, N369H, T431M and D445G (highlighted with grey shading). Within the wrist of monomer 2, there is one amino acid difference; at the homologous position to glycine 391 in hGDF9, hBMP15 contains an arginine (highlighted with an asterisk)

The structure of TGF-β superfamily ligand monomers has been likened to an open hand, with the functional (ie active) mature dimer forming through interactions between the inner portions of the "wrist" and the "palm". The wrist region forms the type 1 receptor binding sites, which are built from amino acids from both monomers of the mature dimer. Structural modelling of the mature human cumulin protein (see FIG. 1A) indicates that the type 1 receptor binding sites on this molecule are different from those found in the hGDF9 and hBMP15 homodimers (Mottershead el al. supra), and that this would appear to explain why cumulin binds ALK4/5 with high affinity leading to the high levels of activity in cumulus cell expansion assays mentioned above. The present Applicant having found that, in contrast to the production of cumulin, it was possible to quite readily produce relatively large quantities of Pro-GDF9, sought to overcome the production difficulties of cumulin by attempting to introduce into the Pro-GDF9 homodimer, wrist regions (ie type I binding sites) the same as or similar to those of cumulin.

Thus, in a first aspect of the present disclosure, there is provided an agent capable of promoting proliferation and differentiation of granulosa cells, said agent comprising a growth and differentiation factor-9 (GDF9) protein comprising a modified GDF9 polypeptide monomer which includes at least one amino acid substitution that enhances binding to and/or activation of activin-like kinase 4 and/or 5 receptor (ALK4/5).

GDF9 genes are highly homologous across mammalian species and encode proteins of very similar size. For instance, the protein encoded by the human GDF9 gene is 454 amino acids (aa) in length, and consists of a signal peptide (aa 1-29), a propeptide (aa 30-318) terminating in a tetrabasic proteolytic processing site (RHRR) followed by the 135 amino acid mature polypeptide (aa 319-454) (McGrath et al. 1995). Similarly, the immature (ie pre-processed) murine GDF9 protein is 441 amino acids in length and includes a signal peptide (aa 1-29), a propeptide (aa 30-306) which terminates in a RRRR proteolytic processing site, and a 135 amino acid mature polypeptide (aa 307-441) (McPherron & Lee 1993); and the immature ovine GDF9 protein is 453 amino acids in length and includes a signal peptide (aa 1-27), a propeptide (aa 28-318) which terminates in a RHRR proteolytic processing site, and a 135 amino acid mature polypeptide (aa 319453). In another example, the immature bovine GDF9 protein is also 453 amino acids in length and includes a signal peptide (aa 1-25), a propeptide (aa 26-318) which terminates in a RHRR proteolytic processing site, and a 135 amino acid mature polypeptide (aa 319-453).

Like other TGF-β superfamily members, the propeptide of GDF9 has an essential role in directing the correct folding, dimerisation, processing and secretion of the mature, biologically active dimeric protein (Gray & Mason 1990) comprising the mature polypeptides. However, somewhat unusually, the two mature polypeptide monomers are not covalently linked (ie by Cys-Cys linkages) and, moreover, it is believed that following cleavage of the propeptide (eg by furin-like proteases) and even secretion from the cell, the propeptide remains non-covalently associated with the mature polypeptides, thereby forming a non-covalent pro/mature complex. This is also considered to be true of BMP15 and cumulin (Mottershead et al., supra); although in the case of BMP15 and cumulin, it appears that at some point, possibly after the propeptide has assisted in presenting the respective mature dimeric protein to its receptor, the propeptide is displaced leaving the mature dimeric protein to stimulate signalling.

Accordingly, as is well known to those skilled in the art, "Pro-GDF9" refers to the pro/mature dimeric complex of GDF9 while "GDF9" refers to the dimeric protein comprising two mature polypeptide monomers (ie without the propeptides). Similarly, "Pro-BMP15" refers to the pro/mature dimeric complex of BMP15 while "BMP15" refers to the dimeric protein comprising two mature BMP15 polypeptide monomers lacking the propeptides. Also, "Pro-cumulin" refers to the pro/mature heterodimeric complex of GDF9 and BMP15 while "cumulin" refers to the heterodimeric protein comprising a mature GDF9 polypeptide monomer and a mature BMP15 polypeptide monomer (ie without the respective propeptides).

Agents according to the first aspect are hereinafter collectively referred to as being "cumulin-like" or termed more specifically as "Cumulin-like GDF9" or "Pro-cumulin-like GDF9", wherein "Cumulin-like GDF9" refers to a dimeric protein comprising two mature GDF9 polypeptide monomers (ie without the propeptides) at least one of which is a "modified GDF9 polypeptide monomer" inasmuch as the polypeptide includes at least one amino acid substitution that enhances binding to and/or activation of activin-like kinase 4 and/or 5 receptor (ALK4/5), and "Pro-cumulin-like GDF9" refers to the pro/mature dimeric complex form of such a protein. It will be appreciated by those skilled in the art that the Pro-cumulin-like GDF9 and Cumulin-like GDF9 molecule may comprise one or two modified GDF9 polypeptide monomer(s).

Where the molecule comprises just one modified GDF9 polypeptide monomer, the other GDF9 polypeptide monomer may be of a wild-type sequence (eg a human wild-type GDF9 mature sequence such as that shown hereinafter as SEQ ID NO: 1, or a murine wild-type GDF9 mature sequence such as that shown hereinafter as SEQ ID NO: 2) or a wild-type sequence incorporating a single "activating" amino acid substitution (eg a human wild-type GDF9 sequence incorporating a Gly-Arg substitution at position 391 or a position corresponding thereto). Such molecules may be considered to be heterodimers.

```
SEQ ID NO: 1:
GQETVSSELKKPLGPASFNLSEYFRQFLLPQNECELHDFRLSFS

QLKWDNWIVAPHRYNPRYCKGDCPRAVCHRYGSPVHTMVQNIIY

EKLDSSVPRPSCVPAKYSPLSVLTIEPDGSIAYKEYEDMIATKC

TCR

SEQ ID NO: 2:
GQKAIRSEAKGPLLTASFNLSEYFKQFLFPQNECELHDFRLSFS

QLKWDNWIVAPHRYNPRYCKGDCPRAVRHRYGSPVHTMVQNIIY

EKLDPSVPRPSCVPGKYSPLSVLTIEPDGSIAYKEYEDMIATRC

TCR
```

On the other hand, where the molecule comprises two modified GDF9 polypeptide monomers, it is to be appreciated that the two modified GDF9 polypeptide monomers may be the same or different. Molecules comprising monomers of the same modified GDF9 polypeptide are homodimers, whereas molecules comprising two different modified GDF9 polypeptide monomers may be considered as heterodimers.

Preferably, the agent of the first aspect comprises a GDF9 protein comprising two monomers of the same modified GDF9 polypeptide monomer (ie a homodimer).

The modified GDF9 polypeptide monomer(s) are preferably derived from human GDF9 (hGDF9) such as wild-type hGDF9 having the amino acid sequence shown as SEQ ID NO: 1, however they may otherwise be derived from the GDF9 proteins of other mammalian species (eg murine GDF9 (mGDF9), ovine GDF9 (oGDF9) and bovine GDF9 (bGDF9)).

The modified GDF9 polypeptide monomer(s) include at least one amino acid substitution that enhances binding to and/or activation of activin-like kinase 4 and/or 5 receptor (ALK4/5). Enhanced binding to and/or activation of ALK4/5 may be determined with reference to the corresponding wild-type GDF9 or Pro-GDF9 protein. For example, where the agent of the first aspect comprises a modified murine GDF9 polypeptide monomer(s), then the amino acid substitution(s) may be assessed for enhanced binding to and/or activation of ALK4/5 by comparative testing against murine Pro-GDF9 or mGDF9 using any of the suitable affinity and/or activity assays known to those skilled in the art, including for example, Surface Plasmon Resonance (SPR) and suitable Smad-2/3 responsive reporter expression assays such as the luciferase-based assay described in the Examples hereinafter. On the other hand, where the agent of the first aspect comprises a modified GDF9 polypeptide monomer(s) developed from a latent GDF9 protein (eg human GDF9), then the amino acid substitution(s) may be assessed for enhanced binding to and/or activation of ALK4/5 by comparative testing against an "activated" Pro-GDF9 or GDF9 from the relevant species (eg one incorporating a single activating amino acid substitution as described in the Examples hereinafter). Enhanced binding to ALK4/5 may be determined by the identification of an increase in binding (eg affinity) to ALK4/5, and enhanced activation of ALK4/5 may be determined by the identification of an increase in Smad-2/3 signalling (which may be observed by increased expression of a reporter from a suitable Smad-2/3 responsive reporter construct).

Preferably, agents according to the first aspect lack an ability to bind to the ALK6 receptor and/or to activate ALK6 to effect Smad-1/5/8 signalling. This may be assessed by using any of the suitable affinity and/or activity assays known to those skilled in the art, including for example, Surface Plasmon Resonance (SPR) and suitable Smad-1/5/8 responsive reporter expression assays such as the luciferase-based assay described in the Examples hereinafter.

Preferably, the modified GDF9 polypeptide monomer includes an amino acid substitution at one or more amino acid positions within "finger 1" which, in hGDF9 for example, spans amino acid positions 354 to 381. More preferably, the modified GDF9 polypeptide monomer includes an amino acid substitution at one or more amino acid positions selected from the group consisting of positions 363, 366 and 369 (from the human wild-type sequence) or corresponding positions of other GDF9 proteins (eg positions 350, 353 and 356 of the murine wild-type sequence). Those skilled in the art can readily identify "corresponding positions" by using, for example, BLAST alignment of the human wild-type sequence with the relevant other GDF9 protein sequence. The amino acid substitution(s) may be an X→Z substitution, wherein X is the "wild-type" amino acid of the particular sequence position, and Z is any other amino acid but preferably one that is selected from the twenty (20) standard amino acids encoded by genetic code. Z may, however, be a non-standard amino acid such as, for example, certain Nα-alkylamino acids (eg N-methyl glycine (sarcosine) and N-methyl alanine), other amino acids such as 2-aminobutyric acid (Abu), amino isobutyric acid, 3-aminoadipic acid (Aad), ornithine, citrulline, amino-oxyserine, homo-arginine, aminosuberic acid and β-2- and β-3-napthylalanine, ring-substituted phenylalanine (Phe) analogues (eg 2,3,4,5,6-pentafluoro-phenylalanine, 4-chloro-phenylalanine, methyl-phenylalanine and phosphono-phenylalanine), phospho-tyrosine (pTyr), selenocysteine and selenomethionine. However, preferably, Z will be an amino acid present in the corresponding position of a BMP15 protein or an otherwise similar amino acid to the one present at the corresponding position of the BMP15 protein. Those skilled in the art can readily identify a "corresponding position of a BMP15 protein" by using BLAST alignment of the mature polypeptide sequences of the relevant GDF9 and BMP15 proteins. Thus, for example, by BLAST alignment between the mature polypeptides of hGDF9 and hBMP15, it can be readily identified that positions 363, 366 and 369 of hGDF9 have corresponding positions in hBMP15 at positions 301, 304 and 307. The amino acids at positions 301, 304 and 307 of hBMP are arginine, glycine and histidine respectively. Accordingly, in some preferred embodiments, the modified GDF9 polypeptide monomer is a modified hGDF9 polypeptide monomer including one or more of the following amino acid substitutions: S363R (ie an Ser-Arg substitution at position 363), K366G (ie a Lys-Gly substitution at position 366) and N369H (ie an Asn-His substitution at position 369). However, the substitution(s) may also be made with other amino acids which are similar to those found in the relevant positions of BMP15. For example, instead of substituting the serine at position 363 of hGDF9 with arginine, a similar amino acid such as lysine, or an amino acid considered to be a conservative substitution of arginine, may be substituted instead.

In some preferred embodiments, the modified GDF9 polypeptide monomer is a modified hGDF9 polypeptide monomer including one or more of the following amino acid substitutions:
(i) S363R, S363K or S363H;
(ii) K366G, K366A, K366V, K366I, K366L or K366M; and
(iii) N369H, N369K or N369R.

In some further preferred embodiments, the modified GDF9 polypeptide monomer is a modified hGDF9 polypeptide monomer including an amino acid substitution from each of the following groups of amino acid substitutions:
(i) S363R, S363K or S363H;
(ii) K366G, K366A, K366V, K366I, K366L or K366M;
(iii) N369H, N369K or N369R; and
(iv) T431M, T431S or T431C.

Preferably, a modified hGDF9 polypeptide monomer will include at least one of the following amino acid substitutions: K366G, K366A, K366V, K366I, K366L and K366M. Most preferably, a modified hGDF9 polypeptide monomer will include at least the amino acid substitution K366G.

Further, in some preferred embodiments, the modified GDF9 polypeptide monomer(s) may include an amino acid substitution to introduce a cysteine residue to achieve disulphide cross-linking (Cys-Cys linkages) of the two monomers of the agent. An agent cross-linked in this manner may show improved levels of stability and/or activity (eg by enhancing binding to and/or activation of ALK4/5). One suitable example of such a substitution is S418C in a modified hGDF9 polypeptide monomer (Mottershead et al. supra). However, those skilled in the art will also understand that the two monomers may be otherwise cross-linked by other chemical cross-linking techniques forming one or more covalent bonds between the monomers, such as the use of carbodiimides such as 1-ethyl-3-(3-dimethylamino propyl)carbodiimide (EDC) to link carboxyl groups and amine groups.

It will also be understood by those skilled in the art that the modified GDF9 polypeptide monomer(s) may include yet further additional amino acid substitutions or other sequence variations such as addition(s) or deletion(s) (eg as may be present in a naturally-occurring variant of the Pro-GDF or GDF9 protein) or which may have been introduced and, preferably, do not substantially alter the function of the polypeptide (eg despite the addition of a further amino acid substitution(s), the polypeptide maintains the ability of binding to and activating ALK4/5). Such variation(s) may include one or more conservative amino acid substitutions such as: G, A, V, I, L, M; D, E; N, Q; S, T; K, R, H; F, Y, W, H; and P, Nα-alkylamino acids. Other substitutions may include the substitution of one or more L-amino acid(s) with a D-amino acid(s). An example of a particular amino acid addition is the addition of a methionine (M) residue to the N-terminal of the polypeptide, as may be a consequence of production of the mature polypeptide by recombinant techniques. Other additions that may be made to, for example, the N-terminal or C-terminal sequence may comprise the addition of short amino acid sequences (eg 2 to 10 amino acids in length) or long amino acid sequences (eg 11 or more amino acids) which confer various additional functionalities or properties, such as improved bioavailability, protein recovery or expression (eg a fusion partner).

Notwithstanding the above, the modified GDF9 polypeptide monomer may additionally or alternatively, comprise amino acid sequences that have been modified either by natural processes, such as post-translational processing, or by chemical modification techniques such as those well known to those skilled in the art (eg Pegylation). Such modifications can occur anywhere in the polypeptide, including within the peptide backbone, the amino acid side-chains and/or the N- and/or C-termini. It will also be appreciated that the same types of modifications may be present in the same or at varying degrees at several sites in the polypeptides. Moreover, other modifications that may be present include the addition of an N-terminal spacer/linker moiety such as β-alanine, 8-amino-3,6-dioxaocanoic acid ("mini-PEG™") and 11-amino-3,6,9-trioxaundecanoic acid ("mini-PEG3™") for attaching, for example, a biochemical tag or chelator such as Fluorescein isothiocyanate (5-FTC), 5-carboxyfluorecein (5-Fam), 5-(and-6)-Carboxytetramethylrhodamine] (5,6-TAMRA), an Alexa Fluor® dye (Life Technologies Corporation, Carlsbad, Calif., United States of America), a cyanine dye, near-IR dye, 1,4,7,10-tetraazacyclododecane-1,4,7,10-tetraacetic acid (DOTA), 2-(4,7-bis(2-(tert-butoxy)-2-oxoethyl)-1,4,7-triazonan-1-yl)acetic acid (NOTA), diethylene triamine pentaacetic acid (DFTA) etc.

Preferably, the agent of the first aspect is provided in an isolated form.

The agent of the first aspect may be produced using synthetic or recombinant techniques well known to those skilled in the art. Where the agent is heterodimeric (ie where the agent comprises two different modified GDF9 polypeptide monomers), the monomers may be produced separately and then simply added together to enable the formation of the dimer. However, it is preferred that the two polypeptide monomers be co-expressed using recombinant techniques.

The agent of the first aspect is capable of promoting proliferation and differentiation of granulosa cells. As such, the agent may be suitable for use in ART such as IVM since, as noted above, the proliferation and differentiation of the granulosa cells into cumulus cells promotes follicular development and oocyte maturation. Moreover, the agent may have a direct effect on oocyte maturation, particularly when in the pro/mature complex form (ie Pro-cumulin-like GDF9) as Pro-cumulin has been observed to promote oocyte development (Mottershead et al. supra), which may lead to enhanced oocyte yield and/or enhanced oocyte quality which, in turn, may result in improved embryo development and foetal survival. For use in an ART, the agent may be formulated into a suitable composition.

Thus, in a second aspect, the present disclosure provides a composition, preferably an aqueous composition, comprising the agent of the first aspect optionally in combination with a pharmacologically acceptable carrier (eg solvent and/or buffer) and/or excipient.

The composition may further comprise one or more other beneficial substances. Examples of suitable beneficial substances include cyclic-AMP (cAMP) modulators which may enhance oocyte development and maturation (Gilchrist et al. 2016).

In a third aspect, the present disclosure provides a method of promoting proliferation and differentiation of granulosa cells (preferably i vitro), said method comprising contacting granulosa cells with an effective amount of the agent of the first aspect or the composition of the second aspect.

In a related fourth aspect, the present disclosure provides the use of an agent of the first aspect or the composition of the second aspect for promoting proliferation and differentiation of granulosa cells.

Further, in a fifth aspect, the present disclosure provides the use of an agent of the first aspect in the manufacture of a composition for promoting proliferation and differentiation of granulosa cells.

In a sixth aspect, the present disclosure provides a method of promoting oocyte maturation (preferably in vitro), said method comprising contacting an immature cumulus-oocyte-complex (COC) with an effective amount of the agent of the first aspect or the composition of the second aspect.

Preferably, the method of the sixth aspect comprises culturing the COC in vitro under conditions favourable to oocyte maturation (for example, in accordance with any of the IVM protocols known to those skilled in the art such as simulated physiological oocyte maturation (SPOM) (Albuz et al., 2010) for a period of, for example, 24 to 40 hours, and the COC is contacted with the agent or composition by adding the agent or composition to the culture media at a suitable time point or time point(s). Preferably, the time point at which the agent or composition is added to the culture media will correspond with the late stage(s) of oocyte maturation, such as the late antral stage (Otsuka et al., 2011).

Preferably, the COC is a human COC.

In some embodiments, the COC has been collected from women suffering from PCOS or POI, other women with pre-existing reproductive issues (such as those associated with hypothalamic dysfunction), or women in remission or recovery from cancer (ie where the administration of exogenous gonadotrophins used in conventional IVF may be undesirable). Further, in some embodiments, the COC is one that has been stored as part of a fertility preservation strategy prior to destructive cancer therapies.

Following maturation of the oocyte in accordance with the method of the sixth aspect, the oocyte may be fertilised according to a standard in vitro fertilisation protocol (eg intracytoplasmic sperm injection (ICSI)), and the fertilised oocyte transferred to a recipient female or placed in appropriate storage for a later transfer.

In a seventh aspect, the present disclosure provides the use of an agent of the first aspect or the composition of the second aspect for promoting oocyte maturation.

In an eighth aspect, the present disclosure provides the use of an agent of the first aspect in the manufacture of a composition for promoting oocyte maturation.

As mentioned above, the agent of the present disclosure may be produced using recombinant techniques well known to those skilled in the art. Accordingly, in a further aspect of the present invention, the invention provides a polynucleotide molecule (preferably in an isolated form) comprising a nucleotide sequence encoding a modified GDF9 polypeptide monomer. In a still further aspect, the present disclosure provides a cloning or expression vector comprising such a polynucleotide molecule. Moreover, in yet a still further aspect, the present disclosure provides a host cell (eg a suitable eukaryotic cell) including the polynucleotide or cloning or expression vector, wherein said host cell is capable, for example, of expressing the agent in culture.

The agent and method(s) of the present disclosure are hereinafter further described by way of the following non-limiting example(s) and accompanying figures.

EXAMPLES

Example 1 Production of hGDF9 Mutants with Amino Acid Substitutions in "Wrist" REGION A comparison of the amino acid sequence of the mature domains of the hGDF9 and hBMP15 proteins of cumulin using BLAST alignment found them to be 59% identical (FIG. 2). To identify the type I receptor binding sites of hGDF9 and hBMP15, an assessment of sequence homology between GDF9, BMP15 and other ligands with known structures was then conducted (Mi et al. 2015). Considering the region in cumulin thought to have high affinity for ALK4/5 (Mottershead et al. supra), it was then observed that hGDF9 and hBMP15 differ by only 5 amino acids (FIG. 2). Using the numbering for hGDF9 these are S363R, K366G, N369H, T431M and D445G.

A number of mutant GDF9 proteins were then designed and produced to determine whether the mature hGDF9 homodimer could be made to be more "cumulin-like" (ie could be modified to achieve higher affinity for ALK4/5) by introducing one or more of the amino acid residues from BMP15. The various mutant proteins are summarised in Table 1 below. All of the mutant proteins incorporated a G391R substitution which overcomes/ameliorates latency of hGDF9 activity (see Example 2).

TABLE 1

| Mutant GDF9 protein name | Mutations included |
|---|---|
| GDF9_G391R | G391R |
| Cumulin-like GDF9 (Mutant 1) | S363R, K366G, N369H, G391R |
| Cumulin-like GDF9_T431M (Mutant 2) | S363R, K366G, N369H, G391R, T431M |
| Cumulin-like GDF9_D445G (Mutant 3) | S363R, K366G, N369H, G391R, D445G |
| Cumulin-like GDF9_T431M_D445G (Mutant 4) | S363R, K366G, N369H, G391R, T431M, D445G |
| Cumulin-like GDF9_R363S (Mutant 5) | K366G, N369H, G391R |
| Cumulin-like GDF9_G366K (Mutant 6) | S363R, N369H, G391R |
| Cumulin-like GDF9_H369N (Mutant 7) | S363R, K366G, G391R |

Materials and Methods
Mutagenesis

The mutant GDF9 proteins were produced by introducing mutations into a codon-optimised expression cassette encoding a modified hGDF9 DNA sequence (hGDF9_His-8; also referred to herein as "wild-type hGDF9") contained within the mammalian expression vector pEF-IRES (Mottershead et al., supra). This modified hGDF9 DNA sequence included sequence encoding the rat serum albumin signal sequence at the 5' end followed by sequences to provide a His-8 tag and a Strep 11 epitope tag at the N-terminus of the GDF9 pro-peptide. Additionally, hGDF9_His-8 included sequence to substitute the usual RHRR tetrabasic proteolytic processing site with RRRR. The QuikChange Lightning Multi Site-Directed Mutagenesis Kit (Agilent Technologies, Inc., Santa Clara, Calif., United States of America) was used to introduce the required mutations. Subsequent changes to the GDF9 mutant cDNA were carried out by overlap extension PCR using Phusion® HF DNA polymerase (New England Biolabs Inc, Ipswich, Mass., United States of America) and the mutated PCR products were ligated into the pEF1α-IRES (Clontech Catalogue no. 631970; Clontech Laboratories, Inc., Mountain View, Calif., United States of America) multiple cloning site A between the restriction sites NheI and EcoRI. For each construct, the entire hGDF9 cDNA cassette was confirmed by DNA sequencing. The primers used for the mutagenesis of hGDF9 His-8 are shown in Table 2.

TABLE 2

| Primer name | Primer purpose | Primer sequence (5'-3') |
|---|---|---|
| CO_hGDF9_5'_NheI | Amplification of hGDF9 from 5' end with NheI site addition | ctaggctagcaccatgaagtgggtaacc tttctcc (SEQ ID NO: 3) |
| CO_hGDF9_3'_EcoRI | Amplification of hGDF9 from 3' end with EcoRI site addition | tgagcggccgcagaattcagt (SEQ ID NO: 4) |
| CO_hGDF9_G391R_S | Introduction of G391R mutation into hGDF9 | ccaagggcagtgagacacagatacggc (SEQ ID NO: 5) |
| CO_hGDF9_G391R_AS | Introduction of G391R mutation into hGDF9 | gccgtatctgtgtctcactgcccttgg (SEQ ID NO: 6) |
| CO_hGDF9_F362-N369_S | Introduction of S363R, K366G and N369H mutations into hGDF9 | GCTGAGCTTCCGCCAGCTGGGGTSGGAC CACTGGATCG (SEQ ID NO: 7) |
| CO_hGDF9_F362-N369_AS | Introduction of S363R, K366G and N369H mutations into hGDF9 | CGATCCAGTGGTCCCACCCCAGCTGGCG GAAGCTCAGC (SEQ ID NO: 8) |
| CO_hGDF9_T431M_S | Introduction of T431M mutation into hGDF9 | CTGAGCGTGCTGATGATCGAGCC (SEQ ID NO: 9) |
| CO_hGDF9_T431M_AS | introduction of T431M mutation into hGDF9 | GGCTCGATCATCACCACGCTCAG (SEQ ID NO: 10) |

TABLE 2-continued

| Primer name | Primer purpose | Primer sequence (5'-3') |
|---|---|---|
| CO_hGDF9_D445G_S | Introduction of D445G mutation into hGDF9 | caaggagtacgagggcatgatcgccac (SEQ ID NO: 11) |
| CO_hGDF9_D445G_AS | Introduction of D445G mutation into hGDF9 | gtggcgatcatgccctcgtactccttg (SEQ ID NO: 12) |

Production and Purification

Production of wild-type and mutant hGDF9 proteins were assessed following transient transfection of HEK-293T cells using polyethylenimine (PEI)-MAX (Polysciences, Inc., Warrington, Pa. United States of America). In brief, HEK-293T cells were plated at $8 \times 10^5$ cells/well in 6-well plates. Wild-type or mutant hGDF9_pEF1α-IRES DNA (2.5 µg/well) was combined with PET for 10 minutes. DNA-PEI complexes were added directly to cells and incubated in OPTI-MEM (Life Technologies, Carlsbad, Calif., United States of America) medium for 4 hours at 37° C. in 5% CO before replacing with fresh OPTI-MEM medium. After 24 hours, the medium was replaced with production media [Dulbecco's modified Eagle medium (DMEM):F12medium containing L-glutamine, 0.02% bovine serum albumin (BSA), 0.005% heparin (Sigma-Aldrich, St Louis, Mo., United States of America)] for 72 hours. Conditioned media was concentrated 5-fold using Nanosep microconcentrators (10 kDa; Pall Life Sciences, Port Washington, N.Y., United States of America). GDF9 expression in media was assessed by Western blotting of reduced samples on 10%/sodium dodecyl sulfate (SDS)-polyacrylamide gel electrophoresis gels (Bio-Rad Laboratories, Inc., Hercules, Calif., United States of America) transferred onto ECL Hybond membranes (GE Health Care, Chalfont St Giles, Bucks, United Kingdom). Blots were probed overnight with mAb 53/1 (1:5000)(Oxford Brookes University, Headington, Oxford, United Kingdom), an antibody specific for a 4 amino acid sequence (EPDG; aa 433-436 in hGDF9) towards the C-terminus of all mammalian mature GDF9 proteins (Gilchrist et al. 2004). This was followed by the secondary antibody horseradish peroxidase-conjugated anti-mouse IgG (1:10,000)(GE Healthcare) with detection using Lumi-light chemiluminescence reagents (Roche, Basel, Switzerland). The pre-stained protein standard SeeBlue Plus2 (Life Technologies) was used to assess molecular weight (MW) sizes.

Larger-scale production of wild-type and mutant hGDF9 proteins was achieved by transfecting multiple 6-well plates at a time with a single construct according to the conditions described above. Each well was treated as a separate transfection, with conditioned media from the hGDF9 mutant transfected cells being pooled after 72 hours incubation. The conditioned media was then centrifuged, concentrated (Centricon Plus-70; Millipore, Billerica, Mass., United States of America), and resuspended in binding buffer (50 mM phosphate buffer, 300 mM NaCl, pH 7.4). The concentrated media was then subjected to immobilised metal affinity chromatography (Co-IMAC) using HisPur™ Cobalt Resin (Thermo Fisher Scientific, Waltham, Mass., United States of America). Bound hGDF9 was then eluted from the Co-IMAC resin using elution buffer (50 mM phosphate buffer, 300 mM NaCl, 333 mM imidazole, pH 7.4). Imidazole was removed from Co-IMAC purified hGDF9 by dialysis against binding buffer using 2 mL 3.5K MW Cut-off Slide-A-Lyzer® MINI Dialysis Devices (Thermo Fisher Scientific) according to the manufacturer's instructions. The degree of recovery and mass estimates for the hGDF9 proteins throughout the purification process was determined by Western blot using recombinant hGDF9 (R&D Systems Inc., Minneapolis, Minn., United States of America) as a reference.

Activity Testing

To test the activity of a selected hGDF9 mutant protein, cells of the COV434 granulosa cell tumour line were transfected with a Smad-2/3 responsive luciferase reporter (pA3-Lux) (Nagarajan et al. 1999) and the transcription factor FAST2 (Chand et al. 2007; Chen el al. 1996). Transfected cells were treated with a dose range (1.6 ng/mL to 25 ng/mL) of Pro-GDF9, Pro-GDF9 plus an equal quantity of Pro-BMP15, Pro-cumulin or the mature hGDF9 mutant protein for ~20 hours. Expression of the luciferase protein was assessed by measuring luminescence immediately after the addition of the substrate D-luciferin (Invitrogen Corporation, Carlsbad, Calif., United States of America). The concentration of cumulin treatments was based on the quantity of GDF9 mature domain in the preparation.

Results

Figure 3:
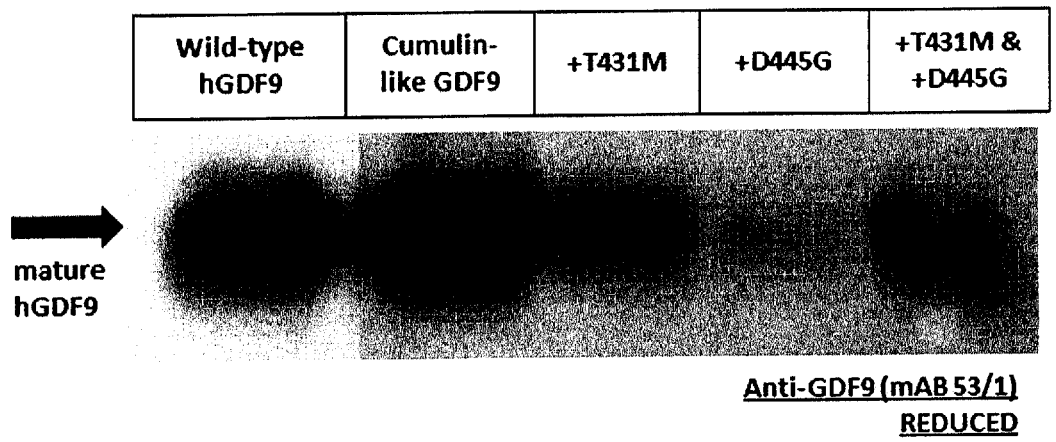
FIG. 3 provides the results of the production of different mature hGDF9 mutant proteins. The cumulin-like GDF9 protein shown is what is termed hereinafter as "cumulin-like GDF9 (Mutant 1)" and incorporates the amino acid substitutions S363R, K366G, N369H and G391R. Other expressed mutant proteins additionally included one or both of the following substitution(s): T431M and D445G.

Expression of hGDF9 Mutants hGDF9 expression cassettes with the desired sequence mutations for the substituted amino acids from hBMP15 were generated using PCR-based site-directed mutagenesis. To assess the expression of hGDF9 mutants, HEK-293T cells were transiently transfected. The conditioned media was collected, concentrated 5× and examined via Western blotting under reducing conditions with an antibody specific to the GDF9 mature peptide (mAB 53/1) (FIG. 3). The mutant GDF9 protein designated in Table 1 as "cumulin-like GDF9 (Mutant 1)" including the amino acid substitutions S363R, K366G, N369H and G391R, was found to be expressed substantially higher than wild-type hGDF9. The addition of subsequent amino acids from hBMP15 (ie the introduction of the further amino acid substitutions T431M and D445G) were found to have a negative effect on expression. Therefore, "Mutant 1" (S363R, K366G, N369H and G391R) was selected for initial activity testing.

Purification of hGDF9 Mutants

Figure 4:
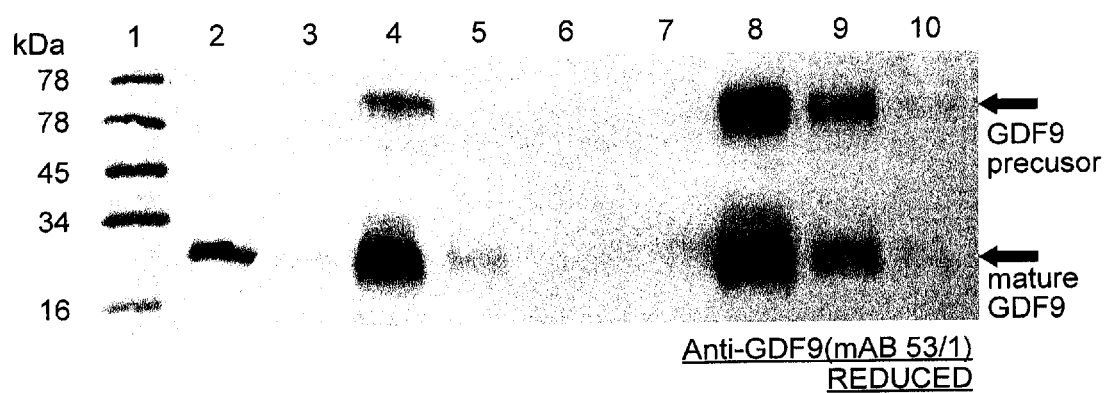
FIG. 4 shows a Western blot providing results of a protein recovery experiment of the cumulin-like GDF9 (Mutant 1) after Co-IMAC purification. Lane contents are detailed in Table 3 hereinafter. The majority of the cumulin-like GDF9 was eluted in a fraction containing 0.33 molar imidazole.

To generate a concentrated and purified preparation of cumulin-like GDF9 (Mutant 1), large scale production was performed by transiently transfecting 8×6-well plates of HEK-293T cells. The conditioned media was then pooled and concentrated to ~1 mL using a Centricon Plus-70 (Millipore) after which binding buffer was used to make it up to a final volume of 5 ml. The concentrated conditioned media was incubated in a column containing ~0.5 mL of HisPur™ Cobalt Resin for ~2 hours at room-temperature whilst rolling. The unbound proteins were collected and the column washed twice with 4 mL of PBS. To elute the bound proteins, the HisPur™ Cobalt Resin was incubated in 3 mL of PBS containing 0.33 molar imidazole for 2 hours at room-temperature whilst rolling. To elute any proteins remaining bound, the HisPur™ Cobalt Resin was then incubated in 3 mL of PBS containing 0.5 molar imidazole for 1 hour at room-temperature whilst rolling. This step was repeated again with PBS containing 1 molar imidazole. The recovery was assessed by Western blot (FIG. 4) probed with mAb 53/1 (1:5000). Gel lanes containing Co-IMAC fractions were loaded with 20 μL (10 μL sample+10 μL 2× reducing dye). Lane contents are as detailed in Table 3.

As the majority of the cumulin-like GDF9 (Mutant 1) protein was eluted in the fraction containing 0.33 molar imidazole, this fraction was dialysed to remove the imidazole. Following dialysis, the concentration of the protein was determined by Western blot using recombinant hGDF9 (R&D Systems) as a reference. The final concentration of the purified cumulin-like GDF9 (Mutant 1) protein was 8.3 ng/L.

TABLE 3

| Lane | Sample |
|---|---|
| 1 | Ladder (SeeBlue Plus2, Life Technologies) |
| 2 | 25 ng standard (R&D Systems rhGDF9) |
| 3 | Conditioned media (Total volume = 96 mL) |
| 4 | Concentrate (Total volume = 5 mL) |
| 5 | Flow-through (Total volume = 5 mL) |
| 6 | PBS Wash #1 (Total volume = 4 mL) |
| 7 | PBS Wash #2 (Total volume = 4 mL) |
| 8 | 333 mM imidazole PBS (Total volume = 3 mL) |
| 9 | 500 mM imidazole PBS (Total volume = 3 mL) |
| 10 | 1M imidazole PBS (Total volume = 3 mL) |

Activity Testing

Figure 5:
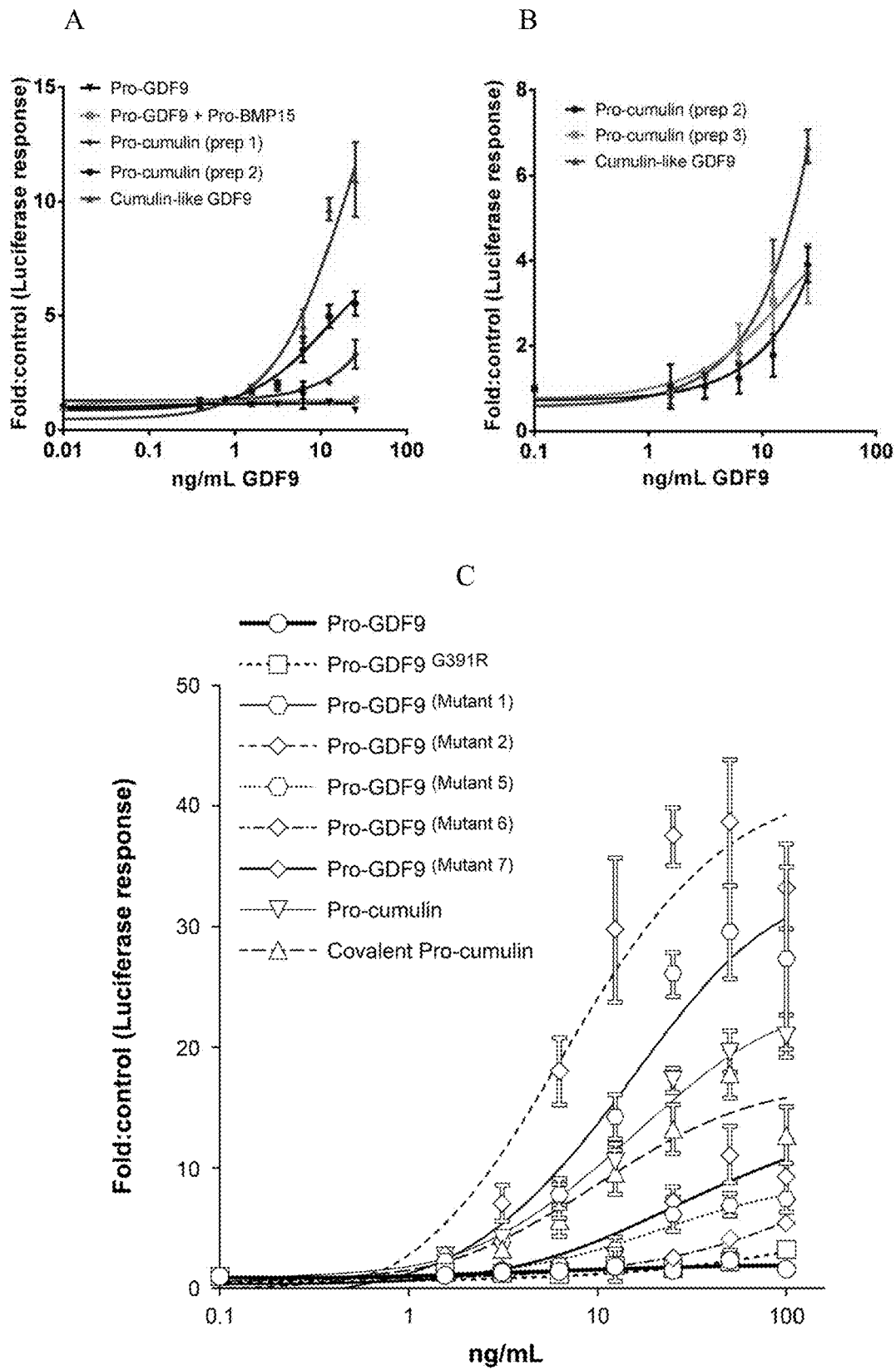
FIG. 5 provides graphical results showing Smad-2/3 activity of Pro-GDF9, cumulin and cumulin-like GDF9 protein preparations: (A) hGDF9 as a non-covalent pro/mature complex (Pro-GDF9) is latent. The addition of independently produced Pro-BMP15 at an equal concentration made no difference (ie there was no increase in expression of a luciferase reporter protein induced by a Smad-2/3 signalling-responsive promoter); (A and B) Pro-cumulin dose-dependently increased the expression of the luciferase reporter protein. The results also showed that the Smad-2/3 activity of different Pro-cumulin preparations is variable, as they also contain latent Pro-GDF9 homodimers and Pro-BMP15 homodimers, with different preparations containing different ratios. In contrast, the cumulin-like GDF9 is a homogenous preparation and was found to consistently induce Smad-2/3 signalling more potently and to a higher degree then Pro-cumulin; (C) experimentation using various cumulin-like GDF9 proteins showed that Mutant 1 and Mutant 2 showed significantly greater levels of expression of the luciferase reporter protein than Pro-cumulin and "Covalent Pro-cumulin" (ie a Pro-cumulin protein with the GDF9 and BMP15 monomers cross-linked by Cys-Cys linkages through introduced cysteine residues in the GDF9 and BMP15 monomers; Mottershead et al. supra)

The results of three representative experiments using the cumulin-like GDF9 (Mutant 1) protein are shown in FIG. 5. It was seen that the luciferase response was maintained at baseline levels after treatment with Pro-GDF9 alone, or when co-treated with an equal concentration of independently produced Pro-BMP15 (FIG. 5A). On the other hand, the Pro-cumulin protein dose-dependently increased the luciferase response, with varying potency and maximal response observed between different batches (FIGS. 5A and 5B). The cumulin-like GDF9 (Mutant 1) protein consistently produced a higher maximal response at the top dose (25 ng/mL), but was also more potent at the lower doses tested (ie 1.6 ng/mL to 12.5 ng/mL)(FIGS. 5A and 5B), but in a further experiment comparing luciferase response with cumulin-like GDF9 (Mutant 2), it was found that a greater response could be achieved with the further inclusion of the T431M substitution (FIG. 5C).

Figure 6:
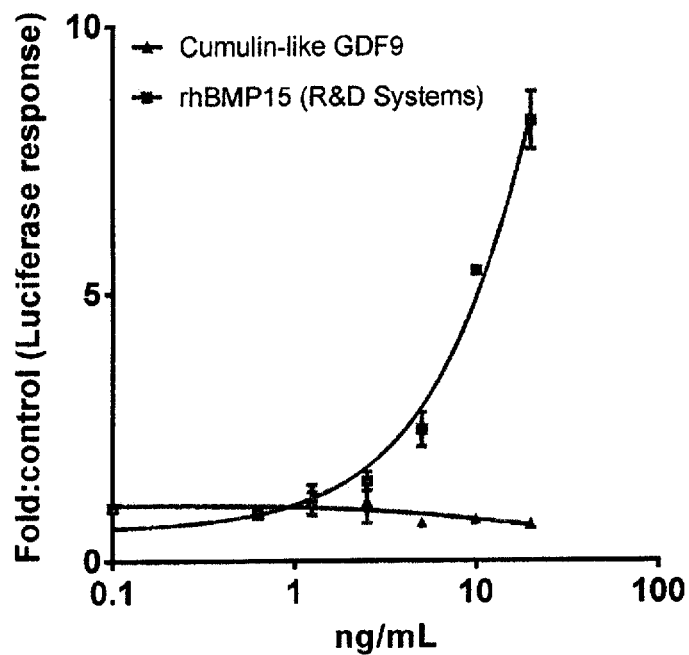
FIG. 6 provides the results of an assay of Smad-1/5/8 activity exhibited by the cumulin-like GDF9 (Mutant 1) protein and a commercially available recombinant hBMP15 protein. The rhBMP15 is able to dose-dependently increase the expression of a luciferase reporter protein which is induced by activation of a Smad-1/5/8 signalling-responsive promoter. In contrast, the cumulin-like GDF9 protein displayed no Smad-1/5/8 activity.

In an alternate luciferase assay, a plasmid with a promoter responsive to Smad-1/5/8 signalling (Korchynskyi and ten Dijke 2002) was transfected into the COV434 granulosa cell tumour line. Transfected cells were then treated with a dose range (0.63 ng/mL to 20 ng/mL) of the cumulin-like GDF9 (Mutant 1) protein or mature recombinant human BMP15 commercially available from R&D Systems (rhBMP15) for ~20 hours. The cumulin-like GDF9 (Mutant 1) protein displayed no ability to activate the promoter, whilst rhBMP15 was observed to dose-dependently increase the expression of the luciferase reporter. The results of a representative experiment are shown in FIG. 6.

DISCUSSION

Mutant mature hGDF9 proteins were expressed incorporating amino acid substitutions which were hoped to confer a more "cumulin-like" activity (ie a higher affinity for ALK45) to the homodimers. One particular mutant, termed cumulin-like GDF9 (Mutant 1) incorporating S363R, K366G, N369H and G391R substitutions, was found to be expressed substantially higher than hGDF9 when expressed alone or in combination with BMP15. It was also found that this mutant could be more readily recovered using a standard purification regime of Co-IMAC and dialysis, than Pro-cumulin. Thus, cumulin-like GDF9 proteins according to the present disclosure appear to offer considerable advantages for production over Pro-cumulin. Moreover, since the expression and purification described in this example resulted in more concentrated final preparations, the cumulin-like GDF9 proteins ought to enable the use of smaller preparation volumes for their potential applications such as the treatment of female infertility (eg where added to a culture media, the reduced preparation volume may limit any adverse effects from the buffer or the addition of impurities).

The cumulin-like GDF9 proteins of the present disclosure also show excellent cumulin-like activity with the representative example (ie cumulin-like GDF9 (Mutant 1)) having the ability to hyper-activate the Smad-2/3 signalling pathway. In fact, in the Smad-2/3 responsive COV434 luciferase assay described in this example, this cumulin-like GDF9 protein proved to work approximately twice as well as Pro-cumulin. While not wishing to be bound by theory, it is considered that this stems from the fact that mature cumulin has one receptor binding site with high affinity for ALK4/5 and another site with affinity for ALK6 (FIG. 1A), whereas the GDF9 homodimer has two ALK4/5 binding sites on opposite sides of the molecule (FIG. 1B). Thus, by introducing amino acid substitutions into the type 1 receptor binding site of GDF9 to make the protein more "cumulin like", it is thought that two high affinity ALK4/5 binding sites have been created in the cumulin-like GDF9 homodimer. Thus, whilst cumulin highly activates one ALK4/5 receptor, a cumulin-like GDF9 protein according to the present disclosure activates two ALK4/5 receptors, thereby doubling the level of Smad-2/3 signalling.

Further, it was observed that the Pro-cumulin preparations displayed substantial batch-to-batch variation in potency, whereas different batches of the cumulin-like GDF9 (Mutant 1) protein, being homogenous preparations of active homodimers, provided a consistent and reliable level of potency.

Example 2 Production of hGDF9 Mutant with a G391R Substitution

The site in cumulin which binds ALK4/5 with high affinity is predicted to be composed of the wrist region of hBMP15 (monomer 1) and the fingers of hGDF9 (monomer 2). Within the wrist of monomer 2, it was observed that there is one amino acid difference; that is, at position 391 in hGDF9 there is a glycine residue whereas the corresponding position of hBMP15 (ie position 329) contains an arginine (see FIG. 2, where this residue is highlighted with an asterisk). It was considered that an arginine in this position may be an important characteristic of active BMP15 molecules (both homo- or hetero-dimers) since, notably, the poorly active murine BMP15 and latent ovine BMP15 lack an arginine in the corresponding position (Al-Musawi el al. supra). In cumulin, an arginine in the corresponding position is not required for activity, but is likely essential to the activity of GDF9 homodimers (Peng et al. 2014; Simpson et al. supra); noting that mature murine GDF9 (which is active) includes arginine at position 391.

Figure 7:
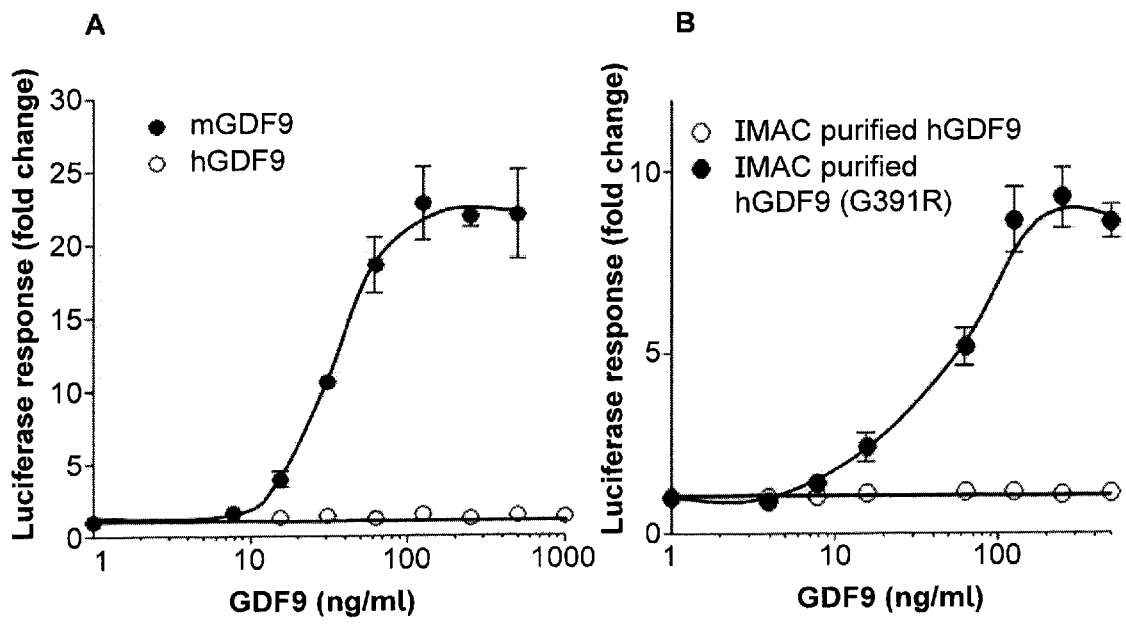
FIG. 7 provides the results of an assay of Smad-2/3 activity of mGDF9, hGDF9 and a hGDF9 (G391R) mutant: (A) mGDF9 and hGDF9—mGDF9 is able to potently and dose-dependently increase the expression of a luciferase reporter protein induced by a Smad-2/3 signalling-responsive promoter, whereas wild-type mature hGDF9 homodimer is inactive even at high concentrations; (B) hGDF9 and hGDF9 (G391R) mutant—mimicking the type I receptor binding site in mGDF9 by substitution of the glycine at residue 391 in hGDF9 with the arginine of mGDF9 (G391R) overcomes the latency of hGDF9. This is demonstrated by the expression of a luciferase reporter protein induced by a Smad-2/3 signalling-responsive promoter. Figure modified from Simpson el al. supra.

Materials and Methods
Mutagenesis
A mutant hGDF9 protein was produced by introducing a mutation to effect a G391R substitution in the manner described in Example 1 for the hGDF9 mutants described therein.
Production and Purification
Expression and purification of the hGDF9 (G391R) mutant was undertaken in a similar manner to that described in Example 1 using transfection of HEK-293T cells and immobilised metal affinity chromatography (Co-IMAC).
Activity Testing
The activity of the hGDF9 (G391R) mutant was tested, along with wild-type mature hGDF9 (R&D Systems) and mature murine GDF9 (R&D Systems), using the Smad-2/3 responsive luciferase reporter and assay described in Example 1. Expression of the luciferase protein was assessed by measuring luminescence immediately after the addition of the substrate D-luciferin (Invitrogen Corporation).
Results
The results of the Smad-2/3 activity testing of the hGDF9 (G391R) mutant is shown in FIG. 7. It was observed that mGDF9 potently and dose-dependently increased the expression of the luciferase reporter protein. In contrast, mature hGDF9 shows no Smad-2/3 activity even at high concentrations (eg >100 ng/ml).
Discussion
In vitro mGDF9 has been shown to exert its biological activity primarily through phosphorylation of Smad-2/3 mediated via the type I receptor activin receptor-like kinase-5 (ALK5) and BMPR2 (Mazerbourg et al. 2004; Vitt et al. 2002). This potently induces the expression of genes essential to cumulus expansion, an important process which successful ovulation and fertilisation depend upon (Li et al. 2008). In contrast to mGDF9, human GDF9 (hGDF9) is secreted as a latent complex (FIG. 1B) consisting of its C-terminal mature domain non-covalently associated with the N-terminal propeptide (Simpson et al. supra). One key difference between the mature proteins of the two species is at residue 391, which is predicted to be within the type I receptor binding site; that is, in hGDF9 this residue is a glycine whereas in mGDF9, there is an arginine at position 391 which as noted above, is also found in the corresponding position of hBMP15. As shown in this example, a single "activating" amino acid substitution may be made to the human GDF9 mature polypeptide sequence to overcome the latency of this protein; that is, by substituting the G391 residue with arginine, the hGDF9 protein can be activated to allow it to induce Smad-2/3 signalling.

Example 3 Production and Analysis of Further hGDF9 Mutants with Cumulin-Like Activity The cumulin-like GDF9 (Mutant 1) protein mutant described in Example 1 includes four mutations (ie S363R, K366G, N369H and G391R). While found to be highly active, it was unclear whether all four mutations were actually required for the heightened activity. In other words, it was considered that it may be that only one of the three "BMP15 residues" (ie S363R, K366G or N369H) was responsible for the observed heightened activity. It was also plausible that if only one of the three mutations was required, then one or both of the other two may even have an inhibitory effect on activity. Therefore, experiments were undertaken to analyse the need for each of S363R, K366G or N369H mutations and determine whether greater levels of activity may be achieved by reversing one or two of these mutations.
Materials and Methods
Mutagenesis
Mutant hGDF9 proteins incorporating the G391R mutation and one "reversed" mutation selected from R363S, G366K and H369N were prepared in the manner described in Example 1. Briefly, three different cumulin-like GDF9 expression cassettes where one mutation from hBMP15 had been reversed were generated using PCR-based site-directed mutagenesis. The primers used are shown in Table 4. The mutants were designated cumulin-like GDF9 R363S, cumulin-like GDF9 G366K and cumulin-like GDF9 H369N. For clarification, cumulin-like GDF9 R363S retained the G391R, K366G and N369H mutations included in the cumulin-like GDF9 (Mutant 1) mutant; cumulin-like GDF9 G366K retained the G391R, S363R and N369H mutations included in the cumulin-like GDF9 (Mutant 1) mutant; and cumulin-like GDF9 H369N retained the G391R, S363R and K366G mutations included in the cumulin-like GDF9 (Mutant 1) mutant.

TABLE 4

| Primer name | Primer purpose | Primer sequence (5'-3') |
| --- | --- | --- |
| CL_GDF9_R363S_S | Reversal of S363R mutation in Cumulin-like GDF9 | cggctgagcctcagccagctgggg (SEQ ID NO: 13) |
| CL_GDF9_R363S_AS | Reversal of S363R mutation in Cumulin-like GDF9 | ccccagctggctgaagctcagccg (SEQ ID NO: 14) |
| CL_GDF9_G366K_S | Reversal of K366G mutation in Cumulin-like GDF9 | cttccgccagctgaagtgggaccactgg (SEQ ID NO: 15) |
| CL_GDF9_G366K_AS | Reversal of K366G mutation in Cumulin-like GDF9 | ccagtggtcccacttcagctggcggaag (SEQ ID NO: 16) |
| CL_GDF9_H369N_S | Reversal of N369H mutation in Cumulin-like GDF9 | ctggggtgggacaactggatcgtgg (SEQ ID NO: 17) |
| CL_GDF9_H369N_AS | Reversal of N369H mutation in Cumulin-like GDF9 | ccacgatccagttgtcccaccccag (SEQ ID NO: 18) |

Production and Purification
Expression and purification of the hGDF9 mutants was undertaken using transfection of HEK-293T cells and immobilised metal affinity chromatography (Co-IMAC) as described in Example 1.

Activity Testing

The activity of the hGDF9 mutants was tested, along with wild-type Pro-hGDF9 and the hGDF9 G391R mutant (Example 2), using the Smad-2/3 responsive luciferase reporter and assay described in Example 1. Expression of the luciferase protein was assessed by measuring luminescence immediately after the addition of the substrate D-luciferin (Invitrogen Corporation).

Results

Expression of hGDF9 Mutants with Reversed Mutations

Figure 8:
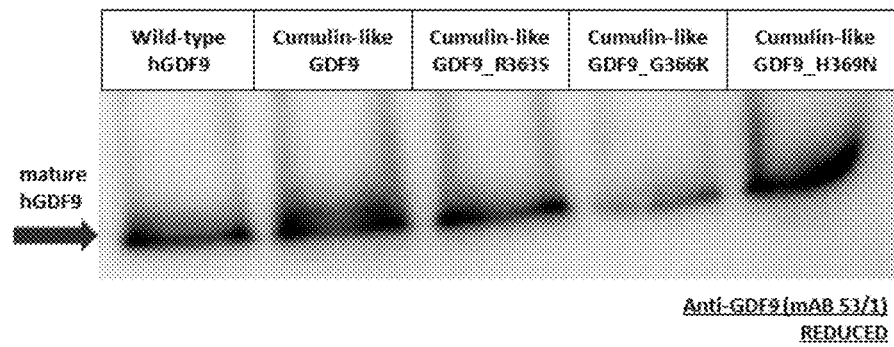
FIG. 8 shows a Western blot of the comparative levels of expression of different, mature "cumulin-like" hGDF9 mutants. The cumulin-like GDF9 (Mutant 1) mutant, designated as "Cumulin-like GDF9" in the figure, contains the G391R mutation as well as S363R, K366G and N369H mutations. This mutant showed increased expression when compared to wild-type hGDF9. Reversal of the S363R mutation caused a small decrease in expression, while reversal of the K366G mutation caused a substantial decrease in expression to levels below that of wild-type hGDF9. In contrast, reversal of the N369H mutation was found to cause a small increase in expression.

To assess the expression of the different cumulin-like GDF9 mutants, conditioned media was collected from the transfected HEK-293T cells culture, concentrated 5× and examined via Western blotting under reducing conditions with an antibody specific to the GDF9 mature protein (mAB 53/1; Oxford Brookes University). The results are shown in FIG. 8. "Reversing" the S363R mutation of the cumulin-like GDF9 (Mutant 1) protein caused a small decrease in expression, while reversal of the K366G mutation caused a more substantial decrease in expression to level. In contrast, the reversal of the N369H mutation caused a small increase in expression.

Activity Testing

Figure 9:
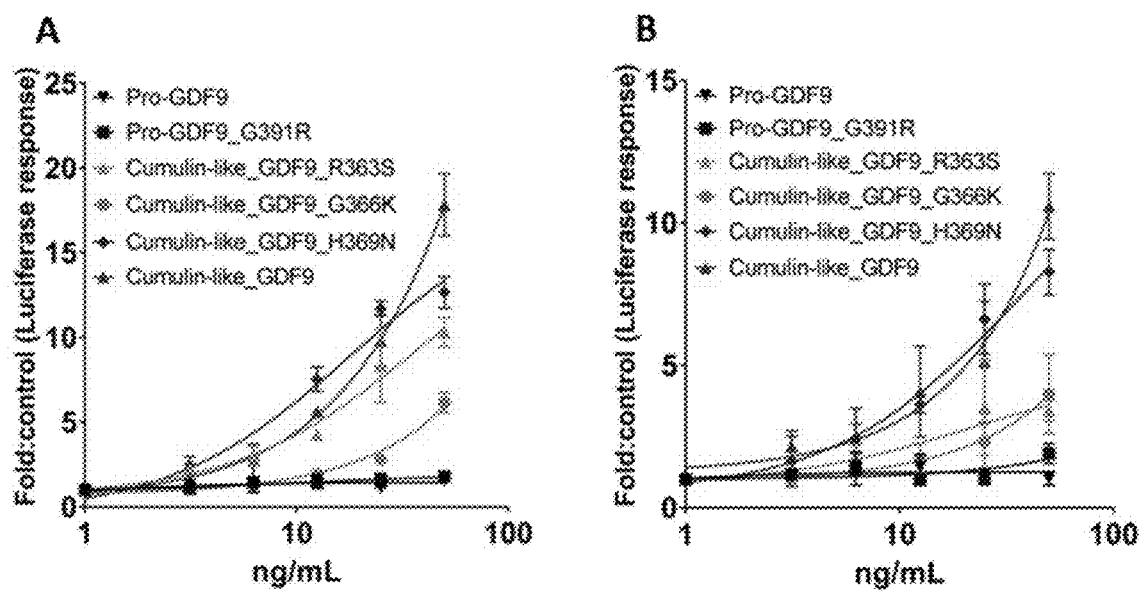
FIG. 9 provides the results of an assay of Smad-2/3 activity of hGDF9 (designated in the figure as Pro-GDF9), the hGDF9 (G391R) mutant (designated as Pro-GDF9_G391R in the figure), the cumulin-like GDF9 (Mutant 1) mutant, and three cumulin-like hGDF9 mutants including reversed mutations found in Cumulin-like GDF9 (Mutant 1) mutant. (A) and (B) show the results of two representative assays using different protein preparations. Reversal of the N369H mutation caused no effect on activity at the lower doses tested (3.1 ng/mL to 25 ng/mL), but did effect the maximal response at 50 ng/mL.

All of the hGDF9 mutants with reversed mutations were purified via Co-IMAC and assessed for activity using COV434 granulosa cells transfected with a Smad-2/3 responsive luciferase reporter (pA3-Lux) and the transcription factor FAST2. Transfected cells were treated with a dose range (3.1 ng/mL to 50 ng/mL) of wild-type Pro-hGDF9, Pro-GDF9_G391R and different Pro-cumulin-like GDF9 variants for ~20 hours. Expression of the luciferase protein was assessed by measuring luminescence immediately after the addition of the substrate D-luciferin (Invitrogen Corporation). The results are shown in FIG. 9. As observed in Example 1, the Pro-cumulin-like GDF9 (Mutant 1) dose-dependently increased the expression of the luciferase reporter protein. Reversing the H369 mutation back to N369 of wild-type hGDF9, caused no effect on activity level at the lower doses tested (3.1 ng/mL to 25 ng/mL), but did effect the maximal response at 50 ng/mL (ie it caused a reduction in activity of about 10% compared to the cumulin-like GDF9 (Mutant 1) protein). On the other hand, reversing either of the S363R and K366G mutations caused much more substantial losses in activity and maximal response (especially noticeable at the higher doses of ≥25 ng/mL).

Discussion

It was found that in order to achieve the activity and maximal response from the cumulin-like GDF9 (Mutant 1) mutant protein, all three of the S363R, K366G and N369H amino acid substitutions (as found in BMP15) were required. Of these, the most important mutation contributing to both expression and activity was identified as K366G. The mutant where this had been reversed (ie Pro-cumulin-like GDF9_G366K) displayed a substantial reduction in expression. More importantly, the Pro-cumulin-like GDF9_G366K mutant displayed less than half the potency of the original Mutant 1 form. It was also found that the reversal of the S363R mutation resulted in a mild decrease in expression and activity. Therefore, it is considered that this mutation also contributes towards the good expression and activity properties of the cumulin-like GDF9 Mutant 1 protein.

Reversal of the N369H mutation (Pro-cumulin-like GDF9_H369N) resulted in a small increase in expression, suggesting that this mutation actually has a negative impact on expression. However, more importantly, the Pro-cumulin-like GDF9_H369N mutant was observed to be highly active. In fact, at most of the doses tested (3.1 ng/mL to 25 ng/mL), this protein showed a comparable level of activity to the Pro-cumulin-like GDF9 (Mutant 1) protein, and only at the highest dose tested (50 ng/mL), was the Pro-cumulin-like GDF9_H369N unable to deliver the same level of activity. Nevertheless, it is considered that the Pro-cummulin-like GDF9_H369N may still be suitable for applications such as those described herein (eg for in vitro maturation (IVM)), noting that it has been reported that the ability of Pro-cumulin to improve IVM outcomes of porcine cumulus-oocyte complexes (COCs) is not significantly different whether the dose used is 20 ng/mL or 100 ng/mL (Mottershead et al. supra), suggesting that the effect of dose during IVM is likely to only be relevant between 0-20 ng/mL.

Example 4 Use of Pro-Cumulin-Like GDF9 in In Vitro Maturation (IVM) of Oocytes

The potential to use a Pro-cumulin-like GDF9 according to the present disclosure to promote follicle development and oocyte maturation and quality (oocyte developmental competence) can be assessed with a granulosa cell proliferation assay and by treating cumulus-oocyte complexes (COCs) during the oocyte in vitro maturation (IVM) phase, followed by in vitro fertilisation and embryo culture and assessment of subsequent blastocyst yield and quality.

Materials and Methods

Granulosa Cell (GC) Proliferation Assay

A murine granulosa cell [3H]-thymidine incorporation assay was performed using standard procedures as previously described (Gilchrist et al. 2004). In brief, mural GCs were collected from C57Bl/6 mice 44-46 h after gonadotropin priming. Cells were then cultured at 37° C. in 5% $CO_2$ in protein-free medium at $2 \times 10^5$ cells/ml with treatments (ie 1.56 ng/ml, 3.125 ng/ml, 6.25 ng/ml and 12.5 ng/ml of Pro-cumulin-like GDF9 (Mutant 2)) for 18 h followed by a further 6 h with 15.4 kBq [3H]-thymidine (PerkinElmer Life Sciences; Waltham, Mass., United States of America). Granulosa cell [3H]-thymidine incorporation was assessed using a Microbeta microplate counter (PerkinElmer Life Sciences) as an indicator of cell DNA synthesis.

Bovine IVM

Bovine cumulus-oocyte-complexes (COCs) were collected from antral follicles from abattoir-derived ovaries in HEPES-buffered tissue culture medium-199 (TCM 199) supplemented with 10% foetal calf serum (FCS; Life Technologies Corporation; Carlsbad, Calif., United States of America) and 4 mg/mL fatty acid-free bovine serum albumin (FAF-BSA; MP BioMedicals; Santa Ana, Calif., United States of America). COCs with an intact cumulus vestment and homogenous cytoplasm were selected and washed in HEPES-TCM-199 supplemented with 50 mg/mL kanamycin, 50 mg/mL heparin and 4 mg/mL FAF-BSA and subsequently washed twice in HEPES-TCM199. COCs were then matured in groups for 24 h (wherein each group is treated with either vehicle (control), or 5 ng/ml, 10 ng/ml or 100 ng/ml of the Pro-cumulin-like GDF9 (Mutant 2)) in bicarbonate-buffered TCM199 supplemented with 0.1 IU/mL hCG (Merck Serono International SA; Darmstadt, Germany), 1 IU/mL recombinant human FSH (Organon International; Oss, Netherlands), 1 µM cysteamine, 10% (w/v) FCS, and 4 mg/mL FAF-BSA under embryo-grade mineral oil in Nunc 4-well dishes (Thermo Fisher Scientific, Inc; Waltham, Mass., United States of America) at 38.5° C. under 5% $CO_2$ and 20% $O_2$. Following the in vitro maturation, oocytes (n=20 per well) were fertilised with sperm from a single sire (Semex Pty Ltd; Melton, VIC, Australia) at a final concentration of $1 \times 10^6$/mL in in vitro fertilisation medium supplemented with amino acids (50 µL) under mineral oil in a 96-well plate (Thermo Fisher Scientific) at 38.5° C. under 5% $CO_2$ in air. Presumptive zygotes are recovered after 23 h, cumulus cells manually stripped and resultant embryos transferred into Nunc 4-well dishes (n=20 per well) containing synthetic oviductal fluid (SOF) medium supplemented with amino acids and 4 mg/mL BSA (500 µL per well). Embryos may then be cultured in a modular incubator at 38.5° C. under 5% 02 and 6% $CO_2$ for 60 h.

Results and Discussion

Granulosa Cell (GC) Proliferation Assay

Figure 10:
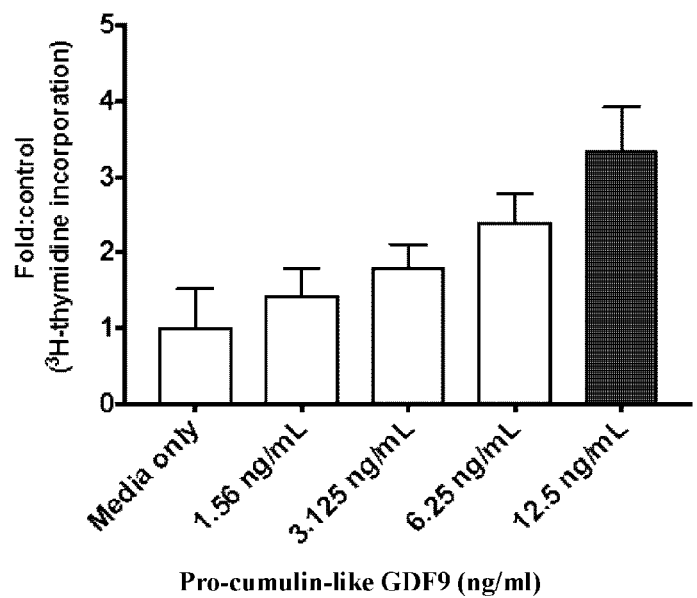
FIG. 10 provides the results of a granulosa cell (GC) proliferation assay, where murine granulosa cells were treated with various amounts of the Pro-cumulin-like GDF9 (Mutant 2). Cell proliferation, as measured by [3H]-thymidine incorporation, showed that treatment of GCs with the Pro-cumulin-like GDF9 promotes the proliferation of the cells in a dose-dependent manner.

Results obtained with the murine GC proliferation assay are shown in FIG. 10. The results showed that the treatment of GCs with the Pro-cumulin-like GDF9 promotes the proliferation of the cells in a dose-dependent manner.

Bovine IVM

Preliminary results obtained from treatments of bovine COCs are shown in Table 5 below. Particularly at 100 ng/ml, the results indicate that treatment of the COCs with the Pro-cumulin-like GDF9 improves the frequency of oocyte fertilisation (% oocyte fertilised) and numbers of occytes compacted on day 5 (% oocyte compacted). It is anticipated that it will also be shown that the treatments with the Pro-cumulin-like GDF9 will also improve the number of blastocysts formed (% blastocysts) and hatched blastocysts (% hatched blastocysts) in the subsequent stages of the IVM.

TABLE 5

| Treatment | Oocyte No. | Fertilised Embryo No. | No. of Compacting Embryos on Day 5 | Fertilised (%) | Compacted (%) |
|---|---|---|---|---|---|
| Control | 72 | 48 | 36 | 66.8 | 49.6 |
| 10 ng Pro-cumulin-like GDF9 | 119 | 69 | 49 | 56.6 | 40.2 |
| 20 ng Pro-cumulin-like GDF9 | 92 | 55 | 40 | 60.8 | 44.8 |
| 100 ng Pro-cumulin-like GDF9 | 101 | 73 | 48 | 76.9 | 53.1 |

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not betaken as, an acknowledgement of any form of suggestion that such prior art forms part of the common general knowledge.

It will be appreciated by those skilled in the art that the agent or method(s) of the present disclosure is not restricted in its particular form or application described. Neither is the agent or method(s) of the present disclosure restricted to any of the preferred embodiment(s) with regard to the particular elements and/or features described or depicted herein. The agent and method(s) may also be the subject of numerous rearrangements, modifications and substitutions without departing from the scope of the present disclosure.

REFERENCES

Albuz F K et al., *Hum Reprod* 25(12):2999-3011 (2010).
Al-Musawi S L et al., *Endocrinology* 154(2):888-899 (2013).
Chand A L et al., *Hum Reprod* 22(12):3241-3248 (2007).
Chen X et al., *Nature* 383(6602):691-6% (1996).
Di Pasquale E et al., *Am J Hum Genet* 75(1):106-111(2004).
Dixit H et al., *Menopause* 12(6):749-754 (2005).
Dong J W et al., *Nature* 383(6600):531-535 (1996).
Fauser, BCJM et al., *Human Reprod Update* 17(6):829-847 (2010).
Gray A M and A L Mason., *Science* 247(4948):1328-1330 (1990).
Gilchrist R B et al., *Biol Reprod* 71:732-739 (2004).
Gilchrist R B., *Reprod Fert Dev* 23(1):23-31 (2011).
Gilchrist R B et al., *Reproduction* 142:647-657 (2011).
Gilchrist R B et al., *Reproduction* 152(5):143-157 (2016).
Korchynskyi O and P ten Dijke, *J Biol Chem* 277(7):4883-4891(2002).
Li Jj et al., *Mol Enducrinol* 29:40-52 (2015).
Li Q L et al., *Mol Cell Biol* 28(23):7001-7011 (2008).
Marchal R et al., *Theriogenology* 57:1523-1532 (2002).
Mazerbourg S et al., *Mol Endocrnol* 18(3):653-665 (2004).
McGrath S A et al., *Mol Endocrinol* 9(1):131-135 (1995).
McIntosh C J et al., *Biol Repd* 79(5):889-896 (2008).
McMahon H E et al., 149(6):2807-2815 (2008).
McNatty K P et al., *Reproduction* 129(4):473-480 (2005).
McPherron A C and S J Lee., *J Biol Chem* 268(5):3444-3449 (1993).
Mi L Z et al., *Proc Natl Acad Sci USA* 112(12):3710-3715 (2015).
Mottershead D G et al., *J Biol Chem* 290(39):24007-24020 (2015).
Nagarajan R P et al., *J Biol Chem* 274(47):33412-33418 (1999).
Otsuka F et al., *J Clin Endocinol Metab* 91(11):4713-4716 (2011).
Patino L C et al., *J Cin Endocrin Metab* 102(3):1009-1019 (2017).
Peng J et al., *Proc Na Acad Sci USA* 110(8):E776-E785 (2013).
Peng J et al., *Biol Reprod* 91(6):7 (2014).
Simpson C M et al., *Endocrinolog* 153(3):1301-1310 (2012).
Smitz J E et al., *Semin Reprod Med* 29(1):24-37 (2011).
Sugimura S et al., *Dev Biol* 403:139-149 (2015).
Vanderhyden B C et al., *Dev Biol* 140:3017-317 (1990).
Vitt U A et al., *Bio Reprod* 67(2):473-480 (2002).
Yoshioka K et al., *J Reprod Dev* 54:208-213 (2008).

What is claimed is:

1. An agent for promoting proliferation and differentiation of granulosa cells, said agent comprising a growth and differentiation factor-9 (GDF9) protein comprising a modified GDF9 polypeptide monomer which includes at least one amino acid substitution that enhances binding to and/or activation of activin-like kinase 4 and/or 5 receptor (ALK4/5), wherein the at least one amino acid substitution that enhances binding to and/or activation of ALK4/5 is at an amino acid position selected from the group consisting of positions 363, 366 and 369 from the human wild-type sequence or corresponding positions of other GDF9 proteins.

2. The agent of claim 1 in a mature dimeric form.

3. The agent of claim 1 in a pro/mature complex form.

4. The agent of claim 1, wherein the GDF9 protein comprises two monomers of the same modified GDF9 polypeptide monomer.

5. The agent of claim 1, wherein the modified GDF9 polypeptide monomer(s) is derived from human GDF9 (hGDF9).

6. The agent of claim 5, wherein the modified hGDF9 polypeptide monomer(s) further includes a G391R amino acid substitution.

7. The agent of claim 1, wherein the at least one amino acid substitution that enhances binding to and/or activation of ALK4/5 is/are selected from the following amino acid substitutions:
(i) S363R, S363K or S363H;
(ii) K366G, K366A, K366V, K366I, K366L or K366M; and
(iii) N369H, N369K or N369R.

8. The agent of claim 1, wherein the modified hGDF9 polypeptide monomer(s) includes an amino acid substitution from each of the following groups of amino acid substitutions:
(i) S363R, S363K or S363H;
(ii) K366G, K366A, K366V, K366I, K366L or K366M;
(iii) N369H, N369K or N369R; and
(iv) T431M, T431S or T431C.

9. An agent comprising a growth and differentiation factor-9 (GDF9) protein comprising a modified GDF9 polypeptide monomer derived from human GDF9 (hGDF9) and which includes at least one of the following amino acid substitutions: K366G, K366A, K366V, K366I, K366L and K366M.

10. The agent of claim 9, wherein the modified GDF9 polypeptide monomer includes a K366G amino acid substitution.

11. The agent of claim 9, wherein the modified GDF9 polypeptide monomer further includes one or more amino acid substitution selected from:
(i) S363R, S363K or S363H; and
(ii) N369H, N369K or N369R.

12. The agent of claim 9, wherein the modified hGDF9 polypeptide monomer includes an amino acid substitution from each of the following groups of amino acid substitutions:
(i) S363R, S363K or S363H;
(ii) K366G, K366A, K366V, K366I, K366L or K366M;
(iii) N369H, N369K or N369R; and
(iv) T431M, T431S or T431C.

13. The agent of claim 9, wherein the modified GDF9 polypeptide monomer further includes a G391R amino acid substitution.

14. The agent of claim 9, wherein the modified GDF9 polypeptide monomer includes the following amino acid substitutions: S363R, K366G, N369H and G391R.

15. The agent of claim 9, wherein the modified GDF9 polypeptide monomer includes the following amino acid substitutions: S363R, K366G, N369H, T431M and G391R.

16. The agent of claim 9, wherein the GDF9 protein comprises two monomers of the same modified GDF9 polypeptide monomer.

17. The agent of claim 1, wherein the modified GDF9 polypeptide monomer further includes an S396C and/or S418C amino acid substitution(s).

18. The agent of claim 1, wherein the agent is provided in an isolated form.

19. A composition comprising the agent of claim 1, optionally in combination with a pharmacologically acceptable carrier and/or excipient.

* * * * *

SEQUENCE LISTING

<160> NUMBER OF SEQ ID NOS: 20

<210> SEQ ID NO 1
<211> LENGTH: 135
<212> TYPE: PRT
<213> ORGANISM: Homo sapiens

<400> SEQUENCE: 1

Gly Gln Glu Thr Val Ser Ser Glu Leu Lys Lys Pro Leu Gly Pro Ala
1               5                   10                  15

Ser Phe Asn Leu Ser Glu Tyr Phe Arg Gln Phe Leu Leu Pro Gln Asn
            20                  25                  30

Glu Cys Glu Leu His Asp Phe Arg Leu Ser Phe Ser Gln Leu Lys Trp
        35                  40                  45

Asp Asn Trp Ile Val Ala Pro His Arg Tyr Asn Pro Arg Tyr Cys Lys
    50                  55                  60

Gly Asp Cys Pro Arg Ala Val Gly His Arg Tyr Gly Ser Pro Val His
65                  70                  75                  80

Thr Met Val Gln Asn Ile Ile Tyr Glu Lys Leu Asp Ser Ser Val Pro
                85                  90                  95

Arg Pro Ser Cys Val Pro Ala Lys Tyr Ser Pro Leu Ser Val Leu Thr
            100                 105                 110

Ile Glu Pro Asp Gly Ser Ile Ala Tyr Lys Glu Tyr Glu Asp Met Ile
            115                 120                 125

Ala Thr Lys Cys Thr Cys Arg
        130                 135

<210> SEQ ID NO 2
<211> LENGTH: 135
<212> TYPE: PRT
<213> ORGANISM: Mus musculus

<400> SEQUENCE: 2

Gly Gln Lys Ala Ile Arg Ser Glu Ala Lys Gly Pro Leu Leu Thr Ala
1               5                   10                  15

Ser Phe Asn Leu Ser Glu Tyr Phe Lys Gln Phe Leu Phe Pro Gln Asn
            20                  25                  30

Glu Cys Glu Leu His Asp Phe Arg Leu Ser Phe Ser Gln Leu Lys Trp
        35                  40                  45

Asp Asn Trp Ile Val Ala Pro His Arg Tyr Asn Pro Arg Tyr Cys Lys
    50                  55                  60

Gly Asp Cys Pro Arg Ala Val Arg His Arg Tyr Gly Ser Pro Val His
65                  70                  75                  80

Thr Met Val Gln Asn Ile Ile Tyr Glu Lys Leu Asp Pro Ser Val Pro
                85                  90                  95

Arg Pro Ser Cys Val Pro Gly Lys Tyr Ser Pro Leu Ser Val Leu Thr
            100                 105                 110

Ile Glu Pro Asp Gly Ser Ile Ala Tyr Lys Glu Tyr Glu Asp Met Ile
            115                 120                 125

Ala Thr Arg Cys Thr Cys Arg
        130                 135

<210> SEQ ID NO 3
<211> LENGTH: 35
<212> TYPE: DNA
<213> ORGANISM: Artificial Sequence
<220> FEATURE:
<223> OTHER INFORMATION: Primer CO_hGDF9_5'_NheI - Amplification of
      hGDF9 from 5' end with NheI site addition

<400> SEQUENCE: 3
ctaggctagc accatgaagt gggtaacctt tctcc                              35

<210> SEQ ID NO 4

```
<211> LENGTH: 21
<212> TYPE: DNA
<213> ORGANISM: Artificial Sequence
<220> FEATURE:
<223> OTHER INFORMATION: Primer CO_hGDF9_3'_EcoRI - Amplification of
      hGDF9 from 3' end with EcoRI site addition

<400> SEQUENCE: 4
tgagcggccg cagaattcag t                                           21

<210> SEQ ID NO 5
<211> LENGTH: 27
<212> TYPE: DNA
<213> ORGANISM: Artificial Sequence
<220> FEATURE:
<223> OTHER INFORMATION: Primer CO_hGDF9_G391R_S - Introduction of G391R
      mutation into hGDF9

<400> SEQUENCE: 5
ccaagggcag tgagacacag atacggc                                     27

<210> SEQ ID NO 6
<211> LENGTH: 27
<212> TYPE: DNA
<213> ORGANISM: Artificial Sequence
<220> FEATURE:
<223> OTHER INFORMATION: Primer CO_hGDF9_G391R_AS - Introduction of
      G391R mutation into hGDF9

<400> SEQUENCE: 6
gccgtatctg tgtctcactg cccttgg                                     27

<210> SEQ ID NO 7
<211> LENGTH: 38
<212> TYPE: DNA
<213> ORGANISM: Artificial Sequence
<220> FEATURE:
<223> OTHER INFORMATION: Primer CO_hGDF9_F362-N369_S - Introduction of
      S363R, K366G and N369H mutations into hGDF9

<400> SEQUENCE: 7
gctgagcttc cgccagctgg ggtgggacca ctggatcg                         38

<210> SEQ ID NO 8
<211> LENGTH: 38
<212> TYPE: DNA
<213> ORGANISM: Artificial Sequence
<220> FEATURE:
<223> OTHER INFORMATION: Primer CO_hGDF9_F362-N369_AS - Introduction of
      S363R, K366G and N369H mutations into hGDF9

<400> SEQUENCE: 8
cgatccagtg gtcccacccc agctggcgga agctcagc                         38

<210> SEQ ID NO 9
<211> LENGTH: 23
<212> TYPE: DNA
<213> ORGANISM: Artificial Sequence
<220> FEATURE:
<223> OTHER INFORMATION: Primer CO_hGDF9_T431M_S - Introduction of T431M
      mutation into hGDF9

<400> SEQUENCE: 9
ctgagcgtgc tgatgatcga gcc                                         23

<210> SEQ ID NO 10
<211> LENGTH: 23
```

```
<212> TYPE: DNA
<213> ORGANISM: Artificial Sequence
<220> FEATURE:
<223> OTHER INFORMATION: Primer CO_hGDF9_T431M_AS - Introduction of
      T431M mutation into hGDF9

<400> SEQUENCE: 10
ggctcgatca tcagcacgct cag                                             23

<210> SEQ ID NO 11
<211> LENGTH: 27
<212> TYPE: DNA
<213> ORGANISM: Artificial Sequence
<220> FEATURE:
<223> OTHER INFORMATION: Primer CO_hGDF9_D445G_S - Introduction of D445G
      mutation into hGDF9

<400> SEQUENCE: 11
caaggagtac gagggcatga tcgccac                                         27

<210> SEQ ID NO 12
<211> LENGTH: 27
<212> TYPE: DNA
<213> ORGANISM: Artificial Sequence
<220> FEATURE:
<223> OTHER INFORMATION: Primer CO_hGDF9_D445G_AS - Introduction of
      D445G mutation into hGDF9

<400> SEQUENCE: 12
gtggcgatca tgccctcgta ctccttg                                         27

<210> SEQ ID NO 13
<211> LENGTH: 24
<212> TYPE: DNA
<213> ORGANISM: Artificial Sequence
<220> FEATURE:
<223> OTHER INFORMATION: Primer CL_GDF9_R363S_S - Reversal of S363R
      mutation in Cumulin-like GDF9

<400> SEQUENCE: 13
cggctgagct tcagccagct gggg                                            24

<210> SEQ ID NO 14
<211> LENGTH: 24
<212> TYPE: DNA
<213> ORGANISM: Artificial Sequence
<220> FEATURE:
<223> OTHER INFORMATION: Primer CL_GDF9_R363S_AS - Reversal of S363R
      mutation in Cumulin-like GDF9

<400> SEQUENCE: 14
ccccagctgg ctgaagctca gccg                                            24

<210> SEQ ID NO 15
<211> LENGTH: 28
<212> TYPE: DNA
<213> ORGANISM: Artificial Sequence
<220> FEATURE:
<223> OTHER INFORMATION: Primer CL_GDF9_G366K_S - Reversal of K366G
      mutation in Cumulin-like GDF9

<400> SEQUENCE: 15
cttccgccag ctgaagtggg accactgg                                        28

<210> SEQ ID NO 16
<211> LENGTH: 28
<212> TYPE: DNA
```

```
<213> ORGANISM: Artificial Sequence
<220> FEATURE:
<223> OTHER INFORMATION: Primer CL_GDF9_G366K_AS - Reversal of K366G
      mutation in Cumulin-like GDF9

<400> SEQUENCE: 16
ccagtggtcc cacttcagct ggcggaag                                          28

<210> SEQ ID NO 17
<211> LENGTH: 25
<212> TYPE: DNA
<213> ORGANISM: Artificial Sequence
<220> FEATURE:
<223> OTHER INFORMATION: Primer CL_GDF9_H369N_S - Reversal of N369H
      mutation in Cumulin-like GDF9

<400> SEQUENCE: 17
ctggggtggg acaactggat cgtgg                                             25

<210> SEQ ID NO 18
<211> LENGTH: 25
<212> TYPE: DNA
<213> ORGANISM: Artificial Sequence
<220> FEATURE:
<223> OTHER INFORMATION: Primer CL_GDF9_H369N_AS - Reversal of N369H
      mutation in Cumulin-like GDF9

<400> SEQUENCE: 18
ccacgatcca gttgtcccac cccag                                             25

<210> SEQ ID NO 19
<211> LENGTH: 105
<212> TYPE: PRT
<213> ORGANISM: Homo sapiens

<400> SEQUENCE: 19

Gln Asn Glu Cys Glu Leu His Asp Phe Arg Leu Ser Phe Ser Gln Leu
1               5                   10                  15

Lys Trp Asp Asn Trp Ile Val Ala Pro His Arg Tyr Asn Pro Arg Tyr
            20                  25                  30

Cys Lys Gly Asp Cys Pro Arg Ala Val Gly His Arg Tyr Gly Ser Pro
        35                  40                  45

Val His Thr Met Val Gln Asn Ile Ile Tyr Glu Lys Leu Asp Ser Ser
    50                  55                  60

Val Pro Arg Pro Ser Cys Val Pro Ala Lys Tyr Ser Pro Leu Ser Val
65                  70                  75                  80

Leu Thr Ile Glu Pro Asp Gly Ser Ile Ala Tyr Lys Glu Tyr Glu Asp
                85                  90                  95

Met Ile Ala Thr Lys Cys Thr Cys Arg
            100                 105

<210> SEQ ID NO 20
<211> LENGTH: 105
<212> TYPE: PRT
<213> ORGANISM: Homo sapiens

<400> SEQUENCE: 20

Asn Asn Gln Cys Ser Leu His Pro Phe Gln Ile Ser Phe Arg Gln Leu
1               5                   10                  15

Gly Trp Asp His Trp Ile Ile Ala Pro Pro Phe Tyr Thr Pro Asn Tyr
            20                  25                  30

Cys Lys Gly Thr Cys Leu Arg Val Leu Arg Asp Gly Leu Asn Ser Pro
```

-continued

```
        35                  40                  45
Asn His Ala Ile Ile Gln Asn Leu Ile Asn Gln Leu Val Asp Gln Ser
    50                  55                  60

Val Pro Arg Pro Ser Cys Val Pro Tyr Lys Tyr Val Pro Ile Ser Val
65                  70                  75                  80

Leu Met Ile Glu Ala Asn Gly Ser Ile Leu Tyr Lys Glu Tyr Glu Gly
                85                  90                  95

Met Ile Ala Glu Ser Cys Thr Cys Arg
                100                 105
```